us US005698574A

United States Patent [19]
Riedl et al.

[11] Patent Number: 5,698,574
[45] Date of Patent: Dec. 16, 1997

[54] 5-MEMBERED HETEROARYL-OXAZOLIDINONES

[75] Inventors: Bernd Riedl; Dieter Häbich; Andreas Stolle, all of Wuppertal, Germany; Hanno Wild, Orange, Conn.; Rainer Endermann, Wuppertal, Germany; Klaus Dieter Bremm, Recklinghausen, Germany; Hein-Peter Kroll, Wuppertal, Germany; Harald Labischinski, Wuppertal, Germany; Klaus Schaller, Wuppertal, Germany; Hans-Otto Werling, Wuppertal, Germany

[73] Assignee: Bayer Aktiengesellschaft, Leverkusen, Germany

[21] Appl. No.: 503,183

[22] Filed: Jul. 17, 1995

[30] Foreign Application Priority Data

Jul. 20, 1994 [DE] Germany .................. P 44 25 613.2

[51] Int. Cl.$^6$ .................................................. C07D 413/00
[52] U.S. Cl. .................... 514/376; 514/340; 514/342; 514/366; 514/367; 546/271.4; 548/148; 548/152; 548/229; 548/232
[58] Field of Search .................... 514/376, 340, 514/342, 366, 367; 546/271.4; 548/229, 232, 148, 152

[56] References Cited

U.S. PATENT DOCUMENTS

| | | | |
|---|---|---|---|
| 2,908,689 | 10/1959 | Gever | 548/299 |
| 4,644,063 | 2/1987 | Masaki et al. | 546/209 |
| 4,705,799 | 11/1987 | Gregory | 514/376 |
| 4,801,600 | 1/1989 | Wang et al. | 514/376 |
| 4,921,869 | 5/1990 | Wang et al. | 514/376 |
| 4,965,268 | 10/1990 | Wang et al. | 514/257 |
| 4,970,217 | 11/1990 | Prücher et al. | 514/327 |
| 5,036,092 | 7/1991 | Wang et al. | 514/516 |
| 5,043,454 | 8/1991 | Wriede et al. | 548/337 |
| 5,254,577 | 10/1993 | Carlson et al. | 514/376 |

FOREIGN PATENT DOCUMENTS

| | | | |
|---|---|---|---|
| 0 300 272 A1 | 1/1989 | European Pat. Off. | |
| 0311090 | 4/1989 | European Pat. Off. | |
| 0312000 | 4/1989 | European Pat. Off. | |
| 0352781 | 1/1990 | European Pat. Off. | |
| 0359418 | 3/1990 | European Pat. Off. | |
| 2304589 | 8/1974 | Germany | 548/229 |
| 57-35589 | 2/1982 | Japan | 548/229 |
| 59-216885 | 12/1984 | Japan | 514/376 |
| WO 93/09103 | 5/1993 | WIPO. | |

OTHER PUBLICATIONS

K.S. Sharma, et al., Indian Journal of Chemistry, vol. 23B, pp. 38–41, (1984).
K.D. Hargrave, et al., J. Med. Chem., vol. 26, No. 8, pp. 1158–1163, (1983).
C-H. Park, et al., J. Med. Chem., vol. 35, No. 6, pp. 1156–1165, (1992).

Primary Examiner—Ralph H. Dean
Attorney, Agent, or Firm—Sprung Kramer Schaeffer & Briscoe

[57] ABSTRACT

The present invention relates to 5-membered heteroaryl-oxazolidinones, to processes for their preparation and to their use as medicaments, in particular as antibacterial medicaments.

6 Claims, No Drawings

5-MEMBERED HETEROARYL-OXAZOLIDINONES

The present invention relates to 5-membered heteroaryl-oxazolidinones, to processes for their preparation and to their use as medicaments, in particular as antibacterial medicaments.

N-aryloxazolidinones having an antibacterial action are known from the publications U.S. Pat. No. 5,254,577, U.S. Pat. No. 4,705,799, EP 311 090, U.S. Pat. No. 4,801,600, U.S. Pat. No 4,921,869, U.S. Pat. No. 4,965,268, EP 312 000 and C. H. Park et al., J. Med. Chem. 35, 1156 (1992).

Oxazolidinones having actions on the central nervous system are known from the publication EP 300 272.

The present invention relates to 5-membered heteroaryl-oxazolidinones of the general formula (I)

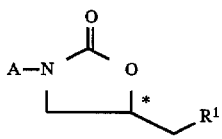

(I)

in which
R$^1$ represents azido or hydroxyl, or represents a group of the formula —OR$^2$, —O—SO$_2$R$^3$ or —NR$^4$R$^5$,
wherein
R$^2$ denotes straight-chain or branched acyl having up to 8 carbon atoms or a hydroxyl-protective group,
R$^3$ denotes straight-chain or branched alkyl having up to 4 carbon atoms or phenyl, which is optionally substituted by straight-chain or branched alkyl having up to 4 carbon atoms,
R$^4$ and R$^5$ are identical or different and cycloalkyl having 3 to 6 carbon atoms, hydrogen, phenyl or straight-chain or branched alkyl having up to 8 carbon atoms or an amino-protective group,
or
R$^4$ or R$^5$ denotes a group of the formula —CO—R$^6$,
wherein
R$^6$ denotes cycloalkyl having 3 to 6 carbon atoms, straight-chain or branched alkyl having up to 8 carbon atoms, phenyl or hydrogen,
A represents a 5-membered aromatic heterocyclic radical which has up to 3 heteroatoms from the series consisting of S, N and/or O, is directly bonded by a carbon atom and can additionally have a fused-on benzene or naphthyl ring, wherein the cyclic radicals are optionally substituted in each case up to 3 times in an identical or different manner by carboxyl, halogen, cyano, mercapto, formyl, trifluoromethyl, nitro, straight-chain or branched alkoxy, alkoxycarbonyl, alkylthio or acyl having in each case up to 6 carbon atoms or by straight-chain or branched alkyl having up to 6 carbon atoms, which can in turn be substituted by hydroxyl, by straight-chain or branched alkoxy or acyl having up to 5 carbon atoms or by a group of the formula —NR$^7$R$^5$,
wherein
R$^7$ and R$^8$ are identical or different and denote hydrogen, straight-chain or branched alkyl having up to 4 carbon atoms or phenyl, or together with the nitrogen atom form a 5- to 6-membered saturated heterocyclic radical which optionally has a further hetero atom from the series consisting of N, S and/or O and can in turn be optionally substituted, including on a further nitrogen atom, by straight-chain or branched alkyl or acyl having up to 3 carbon atoms,
and/or
the cyclic radicals are optionally substituted by a group of the formula —NR$^{7'}$R$^{8'}$,
wherein
R$^{7'}$ and R$^{8'}$ are identical or different and have the abovementioned meaning of R$^7$ and R$^8$ and are identical to or different from these,
and/or
the cyclic radicals are optionally substituted by (C$_2$-C$_8$)-alkenylphenyl, phenyl or by a 5- or 6-membered saturated or unsaturated heterocyclic radical having up to 3 hetero atoms from the series consisting of S, N and/or O, which are in turn optionally substituted by a group of the formula —CO—NR$^9$R$^{10}$, —NR$^{11}$R$^{12}$, —NR$^{13}$—S(O)$_2$—R$^{14}$, R$^{15}$R$^{16}$N—SO$_2$— or R$^{17}$—S(O)$_a$—,
wherein
a denotes the number 0, 1 or 2,
R$^9$, R$^{10}$, R$^{13}$, R$^{15}$ and R$^{16}$ are identical or different and denote hydrogen, straight-chain or branched alkyl having up to 6 carbon atoms or phenyl,
R$^{11}$ and R$^{12}$ are identical or different and have the abovementioned meaning of R$^7$ and R$^8$ and are identical to or different from these,
R$^{14}$ and R$^{17}$ are identical or different and have the abovementioned meaning of R$^3$ and are identical to or different from this,
and/or in turn are optionally substituted up to twice in an identical or different manner by carboxyl, halogen, cyano, mercapto, formyl, trifluoromethyl, nitro, phenyl, straight-chain or branched alkoxy, alkoxycarbonyl, alkylthio or acyl having in each case up to 6 carbon atoms or by straight-chain or branched alkyl having up to 6 carbon atoms, which can in turn be substituted by hydroxyl, by straight-chain or branched alkoxy or acyl having up to 5 carbon atoms or by a group of the formula —NR$^{18}$R$^{19}$,
wherein
R$^{18}$ and R$^{19}$ have the abovementioned meaning of R$^7$ and R$^8$ and are identical to or different from these,
and/or
the cyclic radicals are optionally substituted by a radical of the formula

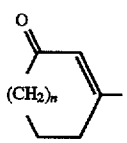

wherein
n denotes the number 0, 1 or 2,
and salts and S-oxides thereof.

The compounds according to the invention can exist in stereoisomeric form which either behaves as mirror images (enantiomers) or do not behave as mirror images (diastereomers). The invention relates to both the enantiomers and diastereomers and to the particular mixtures thereof. The racemic forms, like the diastereomers, can be separated into the stereoisomerically uniform constituents in a known manner.

Physiologically acceptable salts of the 5-membered heteroaryl-oxzolidinones can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts with customary bases may be mentioned as salts, such as, for example, alkali metal salts (for example sodium or potassium salts), alkaline-earth metal salts (for example calcium or magnesium salts) or ammonium salts derived from ammonia or organic amines, such as, for example, diethylamine, triethylamine, ethyldiisopropylamine, procaine, dibenzylamine, N-methylmorpholine, dihydroabiethylamine, 1-ephenamine or methyl-piperidine.

In the context of the invention, a heterocyclic radical under substituent A in the case of direct bonding to the oxazolidinone skeleton represents a 5-membered aromatic ring which can contain up to 3 oxygen, sulphur and/or nitrogen atoms as hetero atoms and can additionally have a fused-on benzene or naphthyl ring. Examples which are mentioned are: pyrrolyl, imidazolyl, furyl, thienyl, thiazolyl, oxazolyl, isothiazolyl, isoxazolyl, furazanyl, indolyl, benzo[b]thienyl, naphtho[2,3-b]thienyl, benzo[b]thiazolyl, benzo[b]furanyl or benzo[b]imidazolyl. Pyrroyl, imidazolyl, furyl, thienyl, isothiazolyl, thiazolyl, isoxazolyl, furazanyl, oxazolyl, benzo[b]thienyl, benzo[b]imidazolyl and benzo[b]thiazolyl are preferred.

In the further field of substitution, a heterocyclic radical also represents a 5- to 6-membered, saturated or unsaturated ring which can contain up to 3 oxygen, sulphur and/or nitrogen atoms as heteroatoms. Preferred rings which are mentioned are: thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl.

These also include 5- to 6-membered saturated heterocyclic rings which are bonded via N and can furthermore contain up to 2 oxygen, sulphur and/or nitrogen atoms as hetero atoms, such as, for example, piperidyl, morpholinyl or piperazinyl or pyrrolidinyl. Piperidyl and pyrrolidinyl are particularly preferred.

Hydroxyl-protective group in the context of the abovementioned definition in general represents a protective group from the series consisting of: trimethylsilyl, triisopropylsilyl, tert-butyldimethylsilyl, benzyl, benzyloxycarbonyl, 2-nitrobenzyl, 4-nitrobenzyl, tert, butyloxycarbonyl, allyloxycarbonyl, 4-methoxybenzyl, 4-methoxybenzyloxycarbonyl, tetrahydropyranyl, formyl, acetyl, trichloroacetyl, 2,2,2-1trichloroethoxycarbonyl, methoxyethoxymethyl, [2-(trimethylsilyl)-ethoxy]methyl, benzoyl, 4-methylbenzoyl, 4-nitrobenzoyl, 4-fluorobenzoyl, 4-chlorobenzoyl or 4-methoxybenzoyl. Acetyl, tert-butyldimethylsilyl and tetrahydropyranyl are preferred.

Amino-protective groups in the context of the present invention are the customary amino-protective groups used in peptide chemistry.

These include, preferably: benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, fluoroenyl-9-methoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl. Preferred compounds are those of the general formula (I) in which $R^1$ represents azido or hydroxyl, or represents a group of the formula —$OR^2$, —$OSO_2R^3$ or —$NR^4R^5$, wherein $R^2$ denotes straight-chain or branched acyl having up to 6 carbon atoms or benzyl, $R^3$ denotes straight-chain or branched alkyl having up to 3 carbon atoms, phenyl or tolyl, $R^4$ and $R^5$ are identical or different and denote cyclopropyl, cyclopentyl, cyclohexyl, hydrogen, phenyl or straight-chain or branched alkyl having up to 6 carbon atoms, tert-butoxycarbonyl or benzyloxycarbonyl, or $R^4$ or $R^5$ denotes a group of the formula —CO—$R^6$, wherein $R^6$ denotes cyclopropyl, cyclobutyl, cyclopentyl, cyclohexyl or straight-chain or branched alkyl having up to 6 carbon atoms, phenyl or hydrogen, A represents pyrrolyl, imidazolyl, furyl, thienyl, thiazolyl, oxazolyl, isothiazolyl, isoxazolyl or furazanyl bonded directly by a carbon atom, or represents indolyl, benzo[b]thienyl, naphtho[2,3-b]thienyl, benzo[b]thiazolyl, benzo[b]imidazolyl or benzo[b]furanyl also bonded directly via a carbon atom of the 5-membered ring, wherein the cyclic radicals are optionally substituted in each case up to 3 times in an identical or different manner by carboxyl, fluorine, chlorine, bromine, iodine, cyano, mercapto, trifluoromethyl, formyl, nitro, straight-chain or branched alkoxy, alkoxycarbonyl, alkylthio or acyl having in each case up to 4 carbon atoms or by straight-chain or branched alkyl having up to 4 carbon atoms, which can in turn optionally be substituted by hydroxyl, by straight-chain or branched alkoxy or acyl having up to 4 carbon atoms or by a group of the formula —$NR^7R^8$, wherein $R^7$ and $R^8$ are identical or different and denote hydrogen, straight-chain or branched alkyl having up to 3 carbon atoms or phenyl, or together with the nitrogen atom form a morpholinyl, pyrrolidinyl, piperazinyl or piperidyl ring which are optionally substituted, including via the free N function, by methyl, ethyl or acetyl, and/or the cyclic radicals are optionally substituted by a group of the formula —$NR^{7'}R^{8'}$, wherein $R^{7'}$ and $R^{8'}$ have the abovementioned meaning of $R^7$ and $R^8$ and are identical to or different from these, and/or the cyclic radicals are optionally substituted by ($C_2$-$C_4$)-alkenylphenyl, phenyl, pyridyl or thienyl, which in turn are optionally substituted by a group of the formula —CO—$NR^9R^{10}$, —$NR^{11}R^{12}$, —$NR^{13}$—$SO_2$—$R^{14}$, $R^{15}R^{16}N$—$SO_2$— or $R^{17}$—$S(O)_a$—, wherein a denotes the number 0, 1 or 2, $R^9$, $R^{10}$, $R^{13}$, $R^{15}$ and $R^{16}$ are identical or different and denote hydrogen, straight-chain or branched alkyl having up to 4 carbon atoms or phenyl, $R^{11}$ and $R^{12}$ are identical or different and have the abovementioned meaning of $R^7$ and $R^8$ and are identical to or different from these, $R^{14}$ and $R^{17}$ are identical or different and have the abovementioned meaning of $R^3$ and are identical to or different from this, and/or in turn are optionally substituted up to twice in an identical or different manner by carboxyl, fluorine, chlorine, bromine, iodine, cyano, mercapto, trifluoromethyl, formyl, nitro, phenyl, straight-chain or branched alkoxy, alkoxycarbonyl, alkylthio or acyl having in each case up to 4 carbon atoms or by straight-chain or branched alkyl having up to 4 carbon atoms, which can in turn be optionally substituted by hydroxyl, by straight-chain or branched alkoxy or acyl having up to 4 carbon atoms or by a group of the formula —$NR^{18}R^{19}$, wherein $R^{18}$ and $R^{19}$ have the abovementioned meaning of $R^7$ and $R^8$ and are identical to or different from these, and/or the cyclic radicals are optionally substituted by a radical of the formula

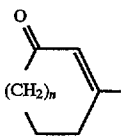

wherein n denotes the number 0, 1 or 2, and salts and S-oxides thereof.

Particularly preferred compounds are those of the general formula (I), in which $R^1$ represents azido or hydroxyl, or represents a group of the formula —$OR^2$, —$OSO_2R^3$ or —$NR^4R^5$, wherein $R^2$ denotes straight-chain or branched acyl having up to 6 carbon atoms, $R^3$ denotes methyl, ethyl, phenyl or tolyl, $R^4$ and $R^5$ are identical or different and denote cyclopropyl, cyclopentyl, cyclohexyl, hydrogen, phenyl or straight-chain or branched alkyl having up to 5 carbon atoms, or $R^4$ or $R^5$ denotes a group of the formula —CO—$R^6$, wherein $R^6$ denotes cyclopropyl, cyclopentyl, cyclohexyl or straight-chain or branched alkyl having up to 4 carbon atoms, hydrogen or phenyl, A represents pyrrolyl, imidazolyl, furyl, thienyl, thiazolyl, isothiazolyl, isoxazolyl, furazanyl or oxazolyl bonded directly via a carbon atom, or represents indolyl, benzo[b]thienyl, benzo[b]imidazolyl, benzo[b]furanyl or benzo[b]thiazolyl likewise bonded directly via a carbon atom of the 5-membered ring wherein the cyclic radicals are optionally substituted in each case up to twice in an identical or different manner by carboxyl, fluorine, chlorine, bromine, iodine, cyano, formyl, trifluoromethyl, nitro, straight-chain or branched alkoxy, alkoxycarbonyl or acyl having in each case up to 4 carbon atoms or by straight-chain or branched alkyl having up to 4 carbon atoms, which can in turn be optionally substituted by hydroxyl, by straight-chain or branched alkoxy or acyl having up to 4 carbon atoms or by a group of the formula —$NR^7R^8$, wherein $R^7$ and $R^8$ are identical or different and denote hydrogen or methyl, or together with the nitrogen atom form a morpholinyl, pyrrolidinyl, piperazinyl or piperidyl ring, which are optionally substituted, including via the free N function, by methyl, ethyl or acetyl, and/or are optionally substituted by a group of the formula —$NR^{7'}R^{8'}$, wherein $R^{7'}$ and $R^{8'}$ have the abovementioned meaning of $R^7$ and $R^8$ and are identical to or different from these, and/or the cyclic radicals are optionally substituted by 2-phenylvinyl, phenyl, pyridyl or thienyl, which are in turn optionally substituted by a group of the formula —CO—$NR^9R^{10}$ or —$NR^{11}R^{12}$, wherein $R^9$ and $R^{10}$ are identical or different and denote hydrogen or methyl, $R^{11}$ and $R^{12}$ are identical or different and have the abovementioned meaning of $R^7$ and $R^8$ and are identical to or different from these, and/or are in turn optionally substituted up to twice in an identical or different manner by carboxyl, fluorine, chlorine, bromine, iodine, cyano, formyl, trifluoromethyl, nitro, phenyl, straight-chain or branched alkoxy, alkoxycarbonyl or acyl having in each case up to 4 carbon atoms or by straight-chain or branched alkyl having up to 4 carbon atoms, which can in turn be optionally substituted by hydroxyl, by straight-chain or branched alkoxy or acyl having up to 4 carbon atoms or by a group of the formula —$NR^{18}R^{19}$, wherein $R^{18}$ and $R^{19}$ have the abovementioned meaning of $R^7$ and $R^8$ and are identical to or different from these, and/or the cyclic radicals are optionally substituted by a radical of the formula

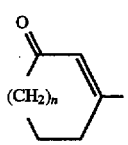

wherein n denotes the number 0, 1 or 2, and salts and S-oxides thereof.

Processes have furthermore been found for the preparation of the compounds of the general formula (I) according to the invention, characterized in that

[A] compounds of the general formulae (II) or (III)

A—N=C=O (II) or A—CO—$N_3$ (III)

in which

A has the abovementioned meanings, are reacted with lithium bromide/$(C_4H_9)_3$ P(O) and epoxides of the general formula (IV)

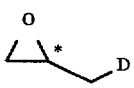 (IV)

in which

D represents $C_1$–$C_6$-acyloxy, in inert solvents, if appropriate in the presence of a base, and in the case where $R^1$=OH, the hydroxyl function is liberated by a typical ester hydrolysis or by a typical transesterification, or

[B] compounds of the general formula (V)

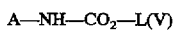

A—NH—CO$_2$—L(V)

in which

A has the abovementioned meaning
and

L represents a typical protective group, preferably benzyl, are reacted in inert solvents and in the presence of a base, for example lithium alkyls or lithium N-alkyl- or lithium N-silylalkylamides, preferably n-butyllithium, with epoxides of the general formula (IV), or

[c] in the case where $R^1$=OH, compounds of the general formula (III) are first converted, by splitting off nitrogen in alcohols, into the compounds of the general formula (Va)

A—NH—CO$_2$—T(Va)

in which

A has the abovementioned meaning
and

T represents straight-chain or branched $C_2$–$C_6$-alkyl, preferably n-butyl, and in a second step these compounds are reacted as described under [A] in inert solvents and in the presence of a base, preferably lithium-N-alkyl- or N-silylalkylamides or n-butyllithium, and epoxides of the general formula (IV), or

[D] compounds of the general formula (VI)

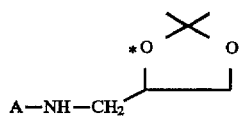

in which

A has the abovementioned meaning, either are reacted directly with acids and diethyl carbonate, or first, by reaction of the compounds of the general formula (VI) with acids, the compounds of the general formula (VII)

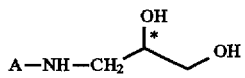

in which

A has the abovementioned meaning are prepared and are then cyclized in the presence of an auxiliary in inert solvents, or

[E] compounds of the general formula (Ia)

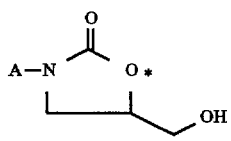

in which

A has the abovementioned meaning are first converted, by reaction with ($C_1$–$C_4$)-alkyl- or phenylsulphonyl chlorides in inert solvents and in the presence of a base, into the corresponding compounds of the general formula (Ib)

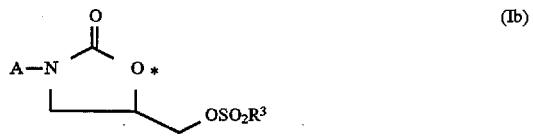

in which

A and $R^3$ have the abovementioned meaning, and the azides of the general formula (Ic)

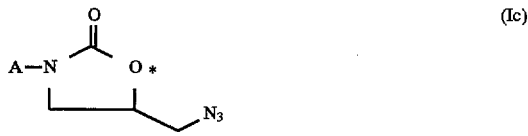

in which

A has the abovementioned meaning, are then prepared with sodium azide in inert solvents, in a further step these are converted, by reaction with ($C_1$–$C_4$–$O_3$)$_3$—P or PPh$_3$, preferably (CH$_3$O)$_3$P, in inert solvents and with acids, into the amines of the general formula (Id)

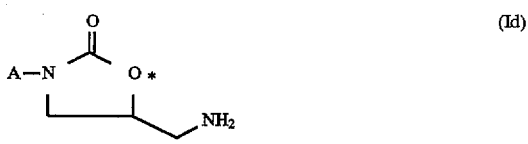

in which

A has the abovementioned meaning, and, by reaction with acetic anhydride or other acylating agents of the general formula (VIII)

$R^{20}$—CO—$R^6$ (VIII)

in which $R^6$ has the abovementioned meaning
and $R^{20}$ represents halogen, preferably chlorine, or represents the radical —O—CO—$R^6$, in inert solvents, the compounds of the general formula (Ie)

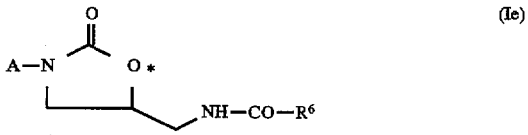

in which

A and $R^6$ have the abovementioned meaning, are prepared, or

[F] compounds of the general formula (Ie) are converted, by halogenation, if appropriate in the presence of a silver catalyst, into the compounds of the general formula (If)

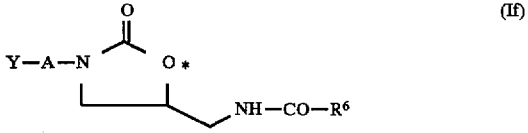

in which

Y represents halogen, preferably bromine or iodine.
and

A and $R^6$ have the abovementioned meaning, or

[G] compounds of the general formula (If) are reacted with compounds of the general formula (IX)

$$A'—R^{21} \qquad (IX)$$

in which

A' represents one of the optionally substituted monocyclic heterocyclic radicals listed above under A, phenyl or $(C_2-C_8)$-alkenylphenyl and $R^{21}$ represents the boronic acid radical —$B(OH)_2$, or represents an organotin radical of the formula —$SnR^{22}R^{23}R^{24}$, wherein $R^{22}$, $R^{23}$ and $R^{24}$ are identical or different and denote $C_1-C_4$-alkyl, in inert solvents and in the presence of a palladium catalyst, and in the case of the S-oxides, an oxidation is carried out, and in the case where $R^4$, $R^5$, $R^9$, $R^{10}$, $R^{11}$, $R^{12}$, $R^{13}$, $R^{15}$, $R^{16}$, $R^{18} \neq H$, an alkylation is carried out by customary methods, and if appropriate further substituents or functional groups which are already present are introduced or, respectively, derivatized by customary methods, such as, for example, redox reactions, substitution reactions and/or hydrolyses or incorporation and removal of protective groups.

The processes according to the invention can be illustrated by way of example by the following equations:

[A]

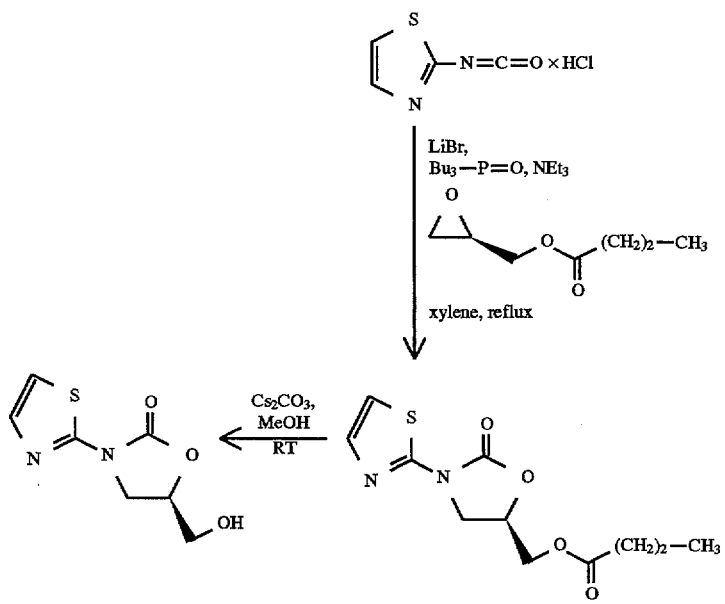

[A]

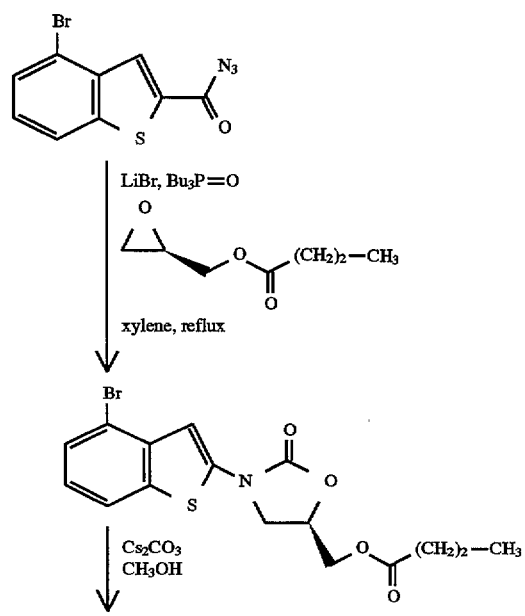

-continued
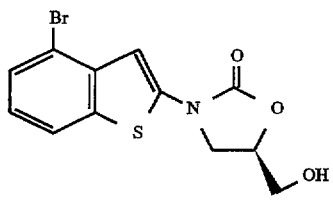
[B]
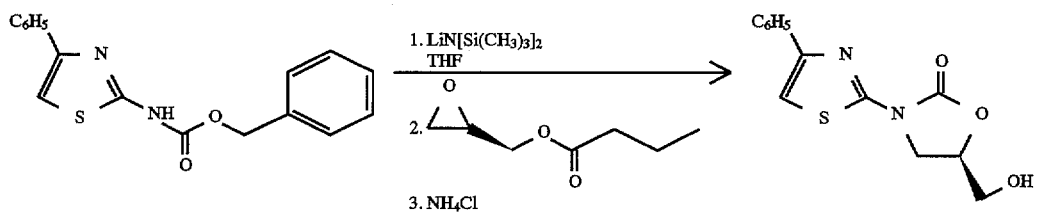
[C]
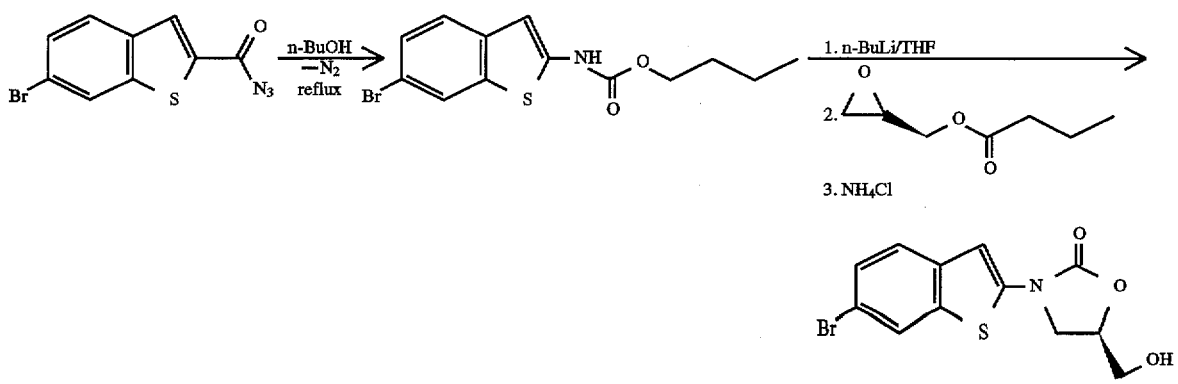
[D]
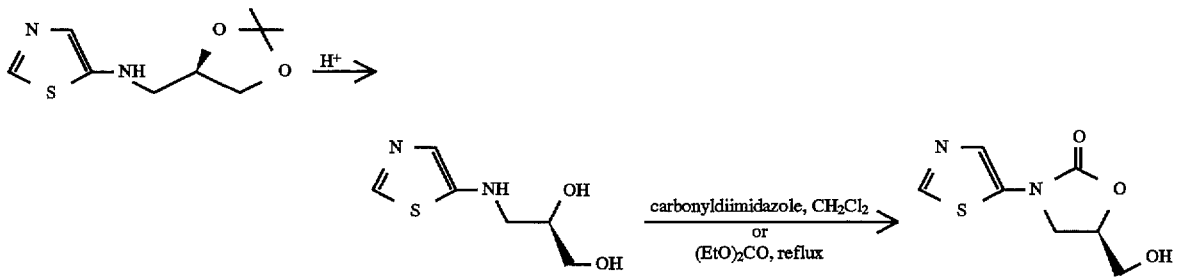
[E]
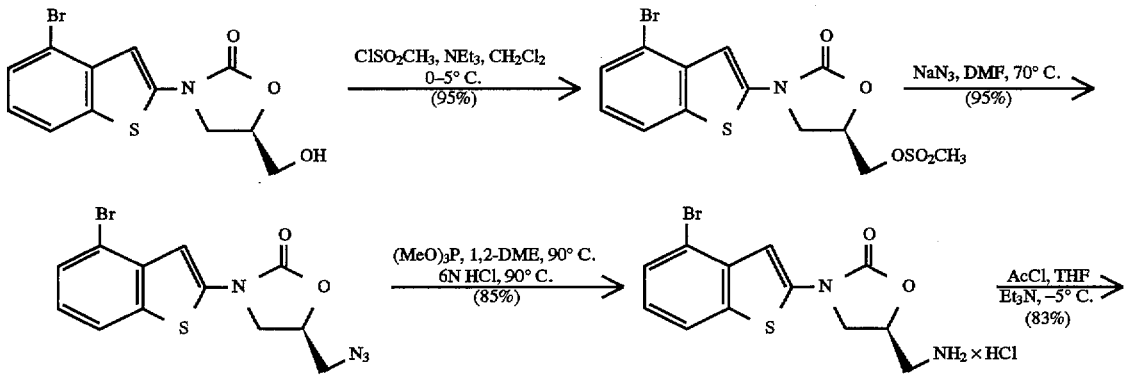

-continued
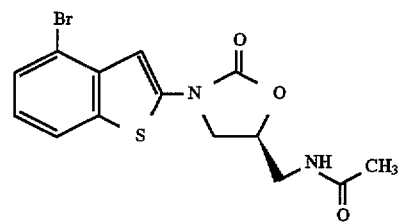
[F]
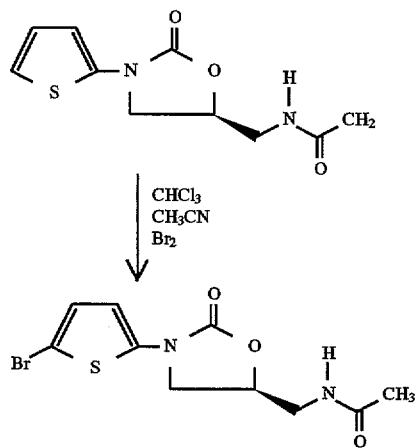
[G]
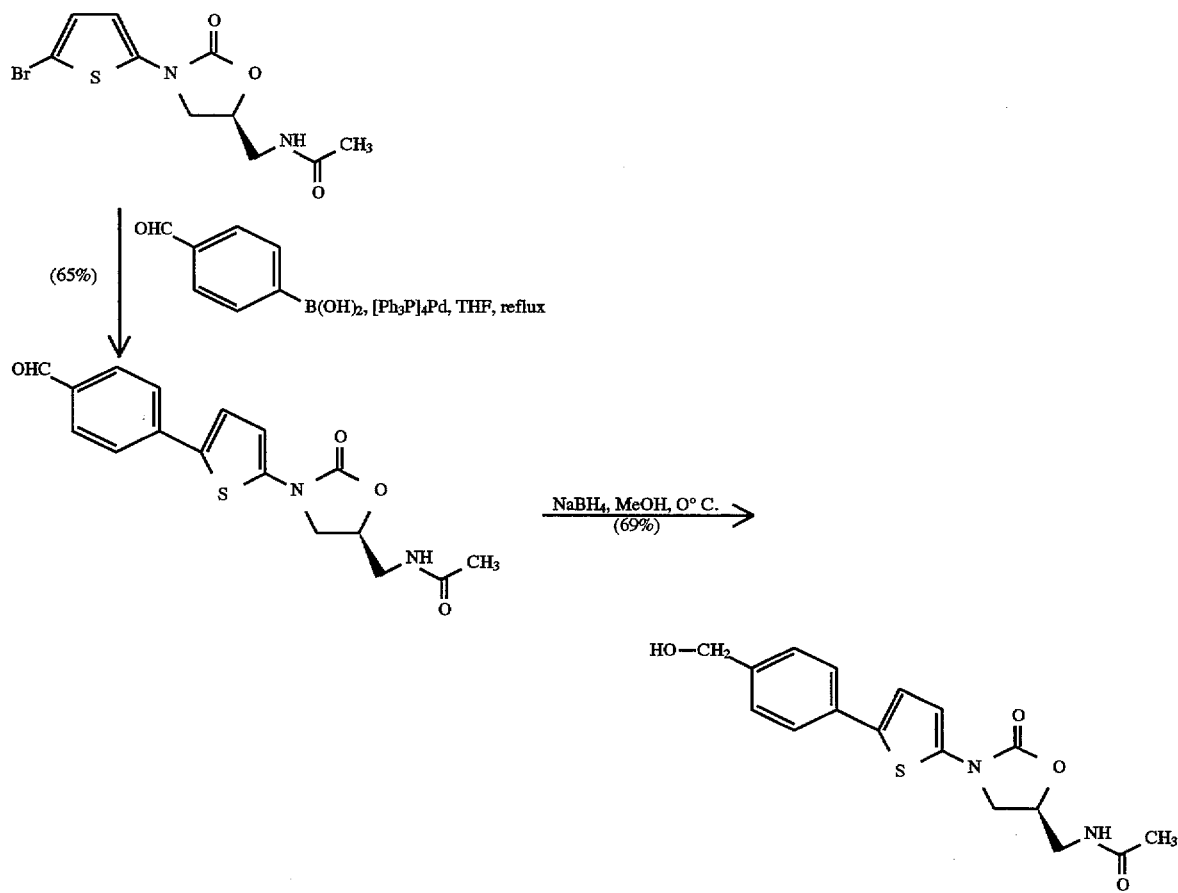

Suitable solvents are, in dependence on the individual process steps, the customary solvents which do not change under the reaction conditions. These include, preferably, alcohols, such as methanol, ethanol, propanol or isopropanol, or ethers, such as diethyl ether, dioxane, 1,2-dimethoxyethane, tetrahydrofuran, glycol dimethyl ether or tert-butyl methyl ether, or ketones, such as acetone or butanone, or amides, such as dimethylformamide or hexamethyl-phosphoric acid triamide, or hydrocarbons, such as hexane, benzene, dichlorobenzene, xylene or toluene, or dimethyl sulphoxide, acetonitrile, ethyl acetate or halogenated hydrocarbons, such as methylene chloride, chloroform or carbon tetrachloride, or pyridine, picoline or N-methylpiperidine. Mixtures of the solvents mentioned can also be used.

Suitable bases are, in dependence on the individual process steps, the customary inorganic or organic bases. These include, preferably, alkali metal hydroxides, such as, for example, sodium hydroxide or potassium hydroxide, or alkali metal carbonates, such as sodium carbonate or potassium carbonate, or alkali metal alcoholates, such as, for example, sodium methanolate or potassium methanolate or sodium ethanolate or potassium ethanolate, or organic amines, such as ethyldiisopropylamine, triethylamine, picoline, pyridine or N-methylpiperidine, or amides, such as sodium amide or lithium diisopropylamide, or lithium N-silylalkylamides, such as, for example, lithium N-(bis)triphenylsilylamide, or lithium alkyls, such as n-butyllithium.

The base is employed in an amount of 1 mol to 10 mol but preferably 1 mol to 3 mol, per mole of the compounds of the general formulae (II), (III), (IV) and (Va).

All the reactions are in general carried out under normal, increased or reduced pressure (for example 0.5 to 5 bar). The reactions are in general carried out under normal pressure.

Process [A] is preferably carried out in xylene or dichlorobenzene, if appropriate in the presence of triethylamine, under reflux.

The base-catalysed transesterification is carried out with one of the abovementioned alcohols, preferably methanol, in a temperature range from −10° C. to +40° C., preferably at room temperature.

Suitable bases are in general sodium bicarbonate, sodium methanolate, hydrazine hydrate, potassium carbonate or caesium carbonate. Caesium carbonate is preferred.

Process [B] is carried out in one of the abovementioned ethers with lithium alkyl compounds or lithium N-silylamides, such as, for example, n-butyllithium, lithium diisopropylamide or lithium bis-trimethylsilylamide, preferably in tetrahydrofuran and lithium bis-trimethylsilylamide or n-butyllithium, in a temperature range from −100° C. to +20° C., preferably from −75° C. to −40° C.

For process [C], the abovementioned alcohols are preferably suitable for the 1st step, and tetrahydrofuran is suitable in the case of the subsequent cyclization.

Suitable bases for the cyclization are preferably the abovementioned lithium N-alkylsilyl compounds or n-butyllithium n-Butyllithium is particularly preferred.

The first reaction step is carried out at the boiling point of the corresponding alcohol, and the cyclization is carried out in a temperature range from −70° C. to room temperature.

The cyclization [D] is carried out in the presence of an auxiliary and/or in the presence of an acid.

Suitable acids are in general inorganic acids, such as, for example, hydrochloric acid or sulphuric acid, or organic carboxylic acids having 1–6 C atoms, which are optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or aryl radicals, such as, for example, methanesulphonic acid, ethanesulphonic acid, benzenesulphonic acid or toluenesulphonic acid. Hydrochloric acid is particularly preferred.

The acid is employed in an amount of 1 mol to 10 mol, preferably 1 mol to 2 mol, per mole of the compounds of the general formula (VI).

Suitable auxiliaries are the customary reagents, such as phosgene, carbonyldiimidazole or diethyl carbonate or trichloromethyl chloroformate. Carbonyldiimidazole, diethyl carbonate or trichloromethyl chloroformate are preferred.

Suitable solvents are the abovementioned halogenated hydrocarbons. Methylene chloride is preferred.

The cyclizations are in general carried out in a temperature range from −20° C. to 100° C., preferably at −20° C. to room temperature.

The acylation [E] is in general carried out in one of the abovementioned ethers or halogenated hydrocarbons, preferably tetrahydrofuran or methylene chloride, in a temperature range from −30° C. to 50° C., preferably from −10° C. to room temperature.

The coupling reactions [G] with the boronic acid compounds and tin aryl compounds are likewise carried out in one of the abovementioned ethers or hydrocarbons, preferably tetrahydrofuran or toluene, and in the presence of a palladium complex.

Suitable palladium complexes are, for example, Pd[P$(C_6H_5)_3]_4$, [$(C_6H_5)_3$P]$_2$PdCl$_2$ or $(C_6H_5CN)_2$PdCl$_2$. [$(C_6H_5)_3$P]$_4$Pd is preferred.

The reaction is carried out in a temperature range from room temperature to 150° C., preferably at the boiling point of the particular solvent.

The reductions are in general carried out with hydrides in inert solvents or with boranes, diboranes or their complex compounds.

The reductions are preferably carried out with hydrides, such as complex borohydrides or aluminium hydrides, as well as boranes. Sodium borohydride, lithium borohydride, sodium cyanoborohydride, lithium aluminium hydride, sodium bis-(2-methoxyethoxy)aluminium hydride or borane tetrahydrofuran are particularly preferably employed here.

The reduction is carried out in general in a temperature range from −50° C. up to the particular boiling point of the solvent, preferably from −20° C. to +90° C.

The reduction can in general be carried out by hydrogen in water or in inert organic solvents, such as alcohols, ethers or halogenated hydrocarbons, or mixtures thereof, with catalysts, such as Raney nickel, palladium, palladium-on-animal charcoal or platinum, or with hydrides or boranes in inert solvents, if appropriate in the presence of a catalyst.

The reaction is preferably carried out with hydrides, such as complex borohydrides or aluminium hydrides. Sodium borohydride, lithium aluminium hydride or sodium cyanoborohydride are particularly preferably employed here.

Suitable solvents here are all the inert organic solvents which do not change under the reaction conditions. These include, preferably, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric acid triamide or dimethylformamide, or acetic acid. It is also possible to use mixtures of the solvents mentioned.

The oxidation to give the S-oxide is in general carried out in one of the abovementioned solvents, preferably in methylene chloride, with oxidizing agents, such as, for example, metachloroperbenzoic acid, hydrogen peroxide or peracetic acid, preferably with metachloroperbenzoic acid, in a temperature range from 0° C. to 80° C., preferably from 20° C. to 60° C.

The hydroxyl-protective groups are in general split off by a customary method, for example by hydrogenolytic cleavage of the benzyl ethers in the abovementioned inert solvents in the presence of a catalyst using hydrogen gas.

The amino-protective group is in general likewise split off by customary methods, and in particular, preferably, Boc is split off with hydrochloric acid in dioxane, Fmoc is split off with piperidine and Z is split off with HBr/HOAc or by hydrogenolysis.

The other derivatization reactions mentioned above are in general carried out by the methods published in Compendium of Organic Synthetic Methods, T. T. Harrison and S. Harrison, Wiley Interscience.

Redox reactions, reductive amination, transesterification and the halogenation of methyl groups with N-bromosuccinimide (NBS) or N-chlorosuccinimide (NCS) are mentioned as preferred and are explained by way of example below.

Suitable solvents for the alkylation are the customary organic solvents which do not change under the reaction conditions. These include, preferably, ethers, such as diethyl ether, dioxane, tetrahydrofuran, glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, acetonitrile, acetone or nitromethane. It is also possible to use mixtures of the solvents mentioned. Methylene chloride, dimethyl sulphoxide and dimethylformamide are preferred.

The alkylation is carried out in the abovementioned solvents at temperatures of 0° C. to 150° C., preferably at room temperatures up to +100° C., under normal pressure.

The amidation and the sulphoamidation are in general carried out in inert solvents in the presence of a base and of a dehydrating agent.

Suitable solvents here are inert organic solvents which do not change under the reaction conditions. These include halogenated hydrocarbons, such as methylene chloride, chloroform, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetonitrile or tetrahydrofuran. It is also possible to employ mixtures of the solvents.

Methylene chloride and tetrahydrofuran are particularly preferred.

Suitable bases for the amidation and the sulphoamidation are the customary basic compounds. These include, preferably, alkali metal and alkaline-earth metal hydroxides, such as lithium hydroxide, sodium hydroxide, potassium hydroxide or barium hydroxide, alkali metal hydrides, such as sodium hydride, alkali metal carbonates or alkaline-earth metal carbonates, such as sodium carbonate or potassium carbonate, or alkali metal alcoholates, such as, for example, sodium methanolate or ethanolate, potassium methanolate or ethanolate or potassium tert-butylate, or organic amines, such as benzyltrimethylammonium hydroxide, tetrabutylammonium hydroxide, pyridine, triethylamine or N-methylpiperidine.

The amidation and the sulphoamidation are in general carried out in a temperature range from 0° C. to 150° C., preferably at 25° C. to 40° C.

The amidation and the sulphoamidation are in general carried out under normal pressure. However, it is also possible to carry out the process under reduced pressure or under increased pressure (for example in a range from 0.5 to 5 bar).

In carrying out the amidation and the sulphoamidation, the base is in general employed in an amount of 1 to 3 mol, preferably 1 to 1.5 mol, per mol of the particular carboxylic acid.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium-3-sulphonate, or propanephosphoric acid anhydride or isobutyl chloroformate or benzotriazolyloxy-tris-(dimethylamino) phosphonium hexafluorophosphate or phosphonic acid diphenyl ester amide or methanesulphonyl chloride, if appropriate in the presence of bases, such as triethylamine or N-ethylmorpholine or N-methylpiperidine or 4-dimethylaminopyridine.

Suitable bases for the hydrolysis are the customary inorganic bases. These include, preferably, alkali metal hydroxides or alkaline-earth metal hydroxides, such as, for example, sodium hydroxide, potassium hydroxide or barium hydroxide, or alkali metal carbonates, such as sodium carbonate or potassium carbonate or sodium bicarbonate. Sodium hydroxide or potassium hydroxide are particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to work under reduced pressure or under increased pressure (for example from 0.5 to 5 bar).

In carrying out the hydrolysis, the base is in general employed in an amount of 1 to 3 mol, preferably 1 to 1.5 mol, per mole of the ester. Molar amounts of the reactants are particularly preferably used.

The esterification is in general carried out with the corresponding alcohols in the presence of acids, preferably sulphuric acid, in a temperature range from 0° C. to 150° C., preferably from 50° C. to 100° C., and at normal pressure.

The compounds of the general formulae (IV), (VIII) and (IX) are known or can be prepared by customary methods.

The compounds of the general formula (VII) are new in most cases and can be prepared, for example, as described above.

The compounds of the general formula (II) are known in some cases or are new, and can then be prepared, for example, by reacting the corresponding amines with trichloroethyl chloroformate in one of the abovementioned solvents, preferably xylene, at the reflux temperature.

The compounds of the general formula (III) are known in some cases or are new, and can then be prepared, for example, starting from ate corresponding carboxylic acids, by reaction either with isobutyl chloroformate/acetone, sodium azide/water or with diphenylphosphoryl azide/ tetrahydrofuran or with xylene or methylene chloride in the presence of one of the abovementioned bases, preferably triethylamine, at −10° C. to room temperature.

The compounds of the general formulae (V) and (Va) are known in some cases or are new, and can be prepared either by splitting off nitrogen from the corresponding carboxylic acid azides and reaction with the corresponding alcohols, or by reaction of the corresponding amines with chloroformic esters, preferably benzyl chloroformate, in one of the abovementioned solvents, preferably tetrahydofuran or dioxane, in a temperature range from −10° C. to 200° C., preferably from 0° C. to 150° C.

The compounds of the general formula (VII) are new in most cases and can be prepared as described above.

The compounds of the general formula (Ia) are new and can be prepared, for example, as described under [A], [B], [D] or [E].

The compounds of the general formula (Ib), (Ic), (Id), (Ie) and (If) are new and can be prepared as described above.

The compounds of the general formula (VI) are known in most cases or are new and can be prepared, for example, starting from the free amines (Ia) by reaction either with the acetonide of glyceraldehyde in methanol and in the presence of sodium acetate/sodium cyanoborohydride or of sodium boranate and methanol in a temperature range from −20° C. to +40° C., preferably from −10° C. to 20° C., under normal pressure.

The halogen atom Y (compounds of the general formula (If)) is introduced in the case of bromine and iodine either with elemental bromine or iodine or in the presence of a silver salt, in one of the abovementioned solvents, preferably methylene chloride, acetonitrile or chloroform, in a temperature range from −30° C. to +60° C., preferably from 0° C. to +30° C., and normal pressure.

Suitable silver salts are, for example, silver tetrafluoroborate, silver trifluoromethanesulphonate or silver trifluoroacetate.

The minimum inhibitory concentrations (MIC) were determined by the series dilution method on Iso-Sensitest agar (Oxoid). A series of agar plates which contained concentration of the active compound which decreased by two-fold dilution in each case was prepared for each test substance. The agar plates were inoculated with a Multipoint inoculator (Denley). Overnight cultures of the pathogens which had been diluted beforehand such that each inoculation point contained about $10^4$ colony-forming particles were used for the inoculation. The inoculated agar plates were incubated at 37° C. and the germ growth was read off alter about 20 hours. The MIC value (µg/ml) indicates the lowest concentration of active compound at which no growth was detectable with the naked eye.

| | | | MIC values (µg/ml): | | | | |
|---|---|---|---|---|---|---|---|
| Ex. No. | Staph 133 | Staph 48N | Staph 25701 | Staph 9TV | E. coli Neumann | Klebs. 57 USA | Psdm. Bonn |
| 22 | 4 | 2 | 1 | 2 | >32 | >32 | >32 |
| 26 | 8 | 8 | 8 | 8 | >32 | >32 | >32 |
| 39 | 2 | 2 | 2 | 1 | >32 | >32 | >32 |
| 40 | 2 | 4 | 2 | 1 | >32 | >32 | >32 |
| 41 | 2 | 2 | 2 | 2 | >32 | >32 | >32 |

-continued

| | | | MIC values (µg/ml): | | | | |
|---|---|---|---|---|---|---|---|
| Ex. No. | Staph 133 | Staph 48N | Staph 25701 | Staph 9TV | E. coli Neumann | Klebs. 57 USA | Psdm. Bonn |
| 42 | 2 | 4 | 4 | 2 | >32 | >32 | >32 |
| 43 | 1 | 1 | 1 | 1 | >32 | >32 | >32 |
| 44 | 0.25 | 0.25 | 0.25 | 0.25 | >32 | >32 | >32 |
| 46 | 2 | 2 | 2 | 0.5 | >32 | >32 | >32 |
| 51 | 4 | 2 | 2 | 1 | >32 | >32 | >32 |
| 56 | 8 | 4 | 4 | 4 | >32 | >32 | >32 |
| 59 | 4 | 2 | 2 | 1 | >32 | >32 | >32 |
| 60 | 16 | 8 | 8 | 8 | >32 | >32 | >32 |
| 101 | 2 | 2 | 2 | 2 | >32 | >32 | >32 |
| 102 | 8 | 8 | 8 | 8 | >32 | >32 | >32 |

The compounds of the general formulae (I), (Ia), (Ib), (Ic), (Id), (Ie) and (If) according to the invention have a broad antibacterial spectrum, specifically against Gram-positive bacteria and Mycobacteria, Corynebacteria, Haemophilus influenzae and anaerobic germs, coupled with a low toxicity. These properties enable them to be used as chemotherapeutic active compounds in human and veterinary medicine.

The compounds according to the invention are active against a broad spectrum of microorganisms. Gram-positive bacteria and bacteria-like microorganisms, such as Mycoplasma, can be controlled and the diseases caused by these pathogens can be prevented, alleviated and/or cured with the aid of the compounds.

The compounds according to the invention are particularly active against bacteria and bacteria-like microorganisms. They are therefore particularly suitable in human and veterinary medicine for prophylaxis and chemotherapy of local and systemic infections caused by such pathogens.

The present invention includes pharmaceutical formulations which, in addition to non-toxic, inert pharmaceutically suitable excipients, comprise one or more compounds according to the invention or which consist of one or more active compounds according to the invention, as well as processes for the preparation of these formulations.

If appropriate, the active compound or compounds can also be in microencapsulated form in one or more of the abovementioned excipients.

The therapeutically active compounds should preferably be present in the abovementioned pharmaceutical formulations in a concentration of about 0.1 to 99.5, preferably about 0.5 to 95% by weight of the total mixture.

In addition to the compounds according to the invention, the abovementioned pharmaceutical formulations can also comprise other pharmaceutical active compounds.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

The new compounds can be combined in the customary concentrations and formulations together with the feed or lactamase inhibitors, for example with penicillins which are particularly resistant to penicillinase and clavulanic acid. Such a combination would be, for example, that with oxacillin or dicloxacillin.

The compounds according to the invention can also be combined with other antibiotics for the purpose of extending the action spectrum and in order to achieve an increase in action.

Appendix to the experimental section
List of the mobile phase mixtures used for the chromatography:

| | |
|---|---|
| I | Methylene chloride : methanol |
| II | Toluene : ethyl acetate |
| III | Acetonitrile : water |
| IV | Ethyl acetate |
| V | Petroleum ether : ethyl acetate |

Abbreviations:

| | |
|---|---|
| Z | Benzyloxycarbonyl |
| Boc | tert-Butyloxycarbonyl |
| DMF | Dimethylformamide |
| Ph | Phenyl |
| Me | Methyl |
| THF | Tetrahydrofuran |
| CDI | Carbonyldiimidazole |
| DCE | Dichloroethane |

Starting compounds

EXAMPLE I

4-Bromo-benzo[b]thiophene-2-carboxylic acid azide

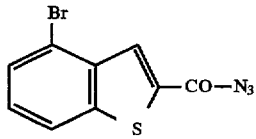

91.2 ml (708 mmol) of isobutyl chloroformate in 500 ml of acetone are slowly added dropwise to a solution, cooled to 0° C., of 140 g (545 mmol) of 4-bromo-benzo[b]thiophene-2-carboxylic acid [Indian J. Chem., Sect. B, 1984, p. 38–41] and 90 ml (643 mmol) of triethylamine in 1120 ml of acetone. The mixture is subsequently stirred at 0° C. for 45 min and 53.8 g (830 mmol) of sodium azide in 270 ml of water are then slowly added dropwise. The preparation is subsequently stirred at 0° C. for 1 hour and then tipped onto 5 l of ice-water. The precipitate which has separated out is filtered off with suction, then rinsed with water and dried in air.

Yield: 116.7 g (76%)

EXAMPLE II (5R)-3-[4-Bromo-benzo[b]thiophenyl]-5-butyryloxymethyl-oxazolidin-2-one

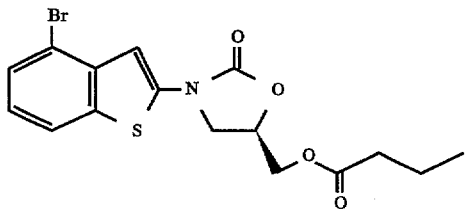

A solution of 3.2 g (38 mmol) of lithium bromide and 8.3 g (38 mmol) of tributylphosphine oxide in 200 ml of xylene is boiled for 1 h using a water separator. A solution of 105 g (372 mmol) of the compound from Example I and 52 ml (372 mmol) of R(–)-glycidyl butyrate in 300 ml of xylene is now added dropwise as quickly as possible at the boiling point (vigorous evolution of gas). When the addition has ended, the mixture is subsequently stirred under reflux for a further 10 min. it is allowed to cool to room temperature and is concentrated. The crude product is chromatographed over silica gel with methylene chloride.

Yield: 44.4 g (30%)

$^1$H-NMR ($D_6$-DMSO, TMS): 7.89 (d, J=7.5 Hz, 1H); 7.58 (d, J=7.5 Hz, 1H); 7.19 (t, J=7.5 Hz, 1H); 6.88 (s, 1H); 5.47–5.54 (m, 1H); 4.72 (d, J=13 Hz, 1H); 4.28–4.48 (m, 2H); 4.0–4.1 (m, 1H); 2.37 (t, J=7.0 Hz, 2H); 1.55 (h, J=7 Hz, 2H); 0.86 (t, J=Hz, 3H). MS (DCI): 398 ($m^+$, 95%), 400 ($M^+$+2, 100%)

EXAMPLE III

2-Benzyloxycarbonylamino-5-bromo-thiazole

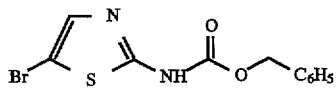

15.1 ml (106 mmol) of benzyl chloroformate are slowly added dropwise to a solution of 25 g (96 mmol) of 2-amino-5-bromothiazole in 100 ml of dioxane and 190 ml of saturated $NaHCO_3$ solution while cooling with ice. The mixture is subsequently stirred overnight at room temperature, the dioxane is evaporated off in vacuo and the solid which has precipitated out is filtered off with suction and rinsed with water and with petroleum ether. The residue is purified over silica gel with methylene chloride/methanol (50:1) as the eluent.

Yield: 17 g (58%)

$^1$H-NMR ($D_6$-DMSO, TMS): 12.62 (s, 1H); 7.47 (s, 1H); 7.40 (m, 5H); 5.23 (s, 2H).

EXAMPLE IV

2-Benzyloxycarbonylamino-4-phenylthiazole

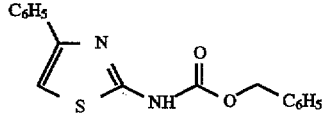

The product is obtained analogously to Example III starting from 2-amino4-phenylthiazole [J. Med. Chem. 26, 1158 (1983)]

$^1$H-NMR ($D_6$-DMSO, TMS): 12.00 (s, 1H); 7.88 (d, J=8 Hz, 2H); 7.60 (s, 1H); 7.37 (m, 8H); 5.26 (s, 2H).

EXAMPLE V

6- Bromo-2-n-butyloxycarbonylamino-benzo[b]thiophene

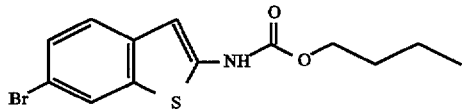

134.4 g (451 mmol) of 6-bromo-benzo[b]thiophene-2-carboxylic acid azide (prepared analogously to Example I) are introduced in portions into 1.6 l of boiling n-butanol (caution, vigorous evolution of gas). When the addition has ended, the mixture is boiled under reflux for a further 10 min and then cooled to room temperature and the n-butanol is stripped off on a rotary evaporator. The residue is stirred in 1 l of petroleum ether/ether (8/2) for 1 hour and filtered off with suction.

Yield: 112 g (76%) Melting point: 115° C.

$^1$H-NMR (D$_6$-DMSO, TMS): 11.04 (s, 1H); 8.08 (d, J=2 Hz, 1H); 7.58 (d, J=7 Hz, 1H); 7.4 (dd, J=7 Hz, J=2 Hz, 1H); 6.8 (s, 1H); 4.16 (t, J=6.5 Hz, 2H); 1.63 (q, J=6.5 Hz, 2H); 1.38 (h, J=6.5 Hz, 2H); 0.92 (t, J=6.5 Hz, 3H).

Preparation Examples

EXAMPLE 1

(5R)-3-[4-Bromo-benzo[b]-thiophenyl]-5-hydroxymethyl-oxazolidin-2-one

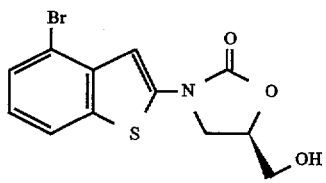

7.14 g (21.9 mmol) of caesium carbonate are added to 44.4 g (109.5 mmol) of the compound from Example II, the mixture is dissolved in 500 ml of methanol and the solution is stirred at room temperature overnight. The solution is concentrated and the residue is stirred with 500 ml of petroleum ether and filtered off with suction. The precipitate is rinsed thoroughly with water and petroleum ether and dried.

Yield: 22 g (61%) Melting point: 203° C.

$^1$H-NMR (D$_6$-DMSO, TMS): 7.9 (d, J=7.5 Hz, 1H); 7.55 (d, J=7.5 Hz, 1H); 7.55 (d, J=7.5 Hz, 1H); 7.17 (t, J=7.15 Hz, 1H); 6.7 (s, 1H); 5.33 (br, 1H); 4.83–4.93 (m, 1H); 4.23 (t, J=9.5 Hz, 1H); 4.0 (dd, J=9.5 Hz, 6.5 Hz, 1H); 3.58–3.80 (m, 2H). $\alpha_D^{20}$=–76.7° (c=0.9, DMSO)

EXAMPLE 2

(5R)-3-(5-Bromo-2-thiazolyl)-5-hydroxymethyl-oxazolidin-2-one

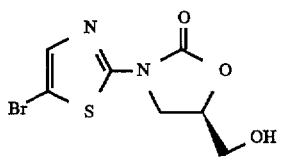

15.6 g (49.5 mmol) of the compound from Example III are suspended in 125 ml of absolute tetrahydrofuran. 59.6 ml of a 1M solution of lithium bis-trimethylsilylamide in tetrahydrofuran are added at –78° C., and the mixture is warmed to 0° C. for 15 min and cooled again to –78° C. 13.9 ml (99.5 mmol) of (R)-glycidyl butyrate are then added and the mixture is subsequently stirred for 18 h, whereupon the reaction solution slowly comes to room temperature. The resulting precipitate is filtered off with suction, the filtrate is diluted with methylene chloride and washed with saturated ammonium chloride solution and the aqueous phase is washed three times with methylene chloride. The combined organic phases are dried (MgSO$_4$) and concentrated. The resulting residue and the product-containing precipitate obtained above are chromatographed over silica gel with toluene/ethyl acetate (5:1→1:1). 1.91 g of product and 6.06 g of the butyrate of the product are obtained. This ester is dissolved in 24 ml of methanol, 1.16 ml (24 mmol) of hydrazine hydrate are added and the mixture is stirred at room temperature for 4 h. It is concentrated to give a further fraction of product. All the product-containing fractions are triturated with ether and the resulting solid is filtered off with suction and dried.

Yield: 3.07 g (23.5%)

$^1$H-NMR (D$_6$-DMSO, TMS): 7.59 (s, 1H); 5.27 (t, J=5 Hz, 1H); 4.87 (m, 1H); 4.18 (t, J=9 Hz, 1H); 3.94 (dd, J=9.6 Hz, 1H); 3.72 (m, 1H); 3.57 (m, 1H).

EXAMPLE 3

(5R)-3-(4-Phenyl-2-thiazolyl)-5-hydroxymethyloxazolidin-2-one

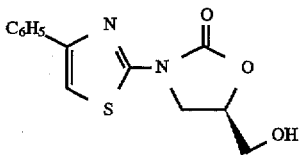

11.6 ml of a 2.5N n-butyllithium solution in hexane are added to 10 g (32.2 mmol) of the compound from Example IV in 80 ml of absolute tetrahydrofuran at –78° C. The mixture is allowed to warm to –30° C. and is then cooled again to –78° C., and 4.05 ml (29 mmol) (R)-glycidyl butyrate are added. The mixture is subsequently stirred for 18 h, whereupon the reaction solution warms to room temperature. For working up, the solution is diluted with methylene chloride and washed with saturated ammonium chloride solution and the aqueous phase is extracted three times with methylene chloride. The organic phases are combined, dried (MgSO$_4$) and concentrated. The residue is purified over silica gel with toluene/ethyl acetate (20:1→1:1) as the eluent.

Yield: 4.75 g (53.5%) Melting point: 156° C. (ether)

$^1$H-NMR (D$_6$-DMSO, TMS): 7.93 (d, J=8 Hz, 2H); 7.71 (s, 1H); 7.5–7.30 (m, 3H); 5.28 (t, J=5 Hz, 1H); 4.77 (m, 1H); 4.32 (t, J=9 Hz, 1H); 4.13 (dd, J=9.6 Hz, 1H); 3.73 (m, 1H); 3.62 (m, 1H). $[\alpha]_D^{20}$=–90.2° (c=0.5, DMSO) MS (EI): m/e=276 (M$^+$), 134 (100%)

EXAMPLE 4

(5R)-3-[6-Bromo-benzo[b]-thiophenyl]-5-hydroxymethyl-oxazolidin-2-one

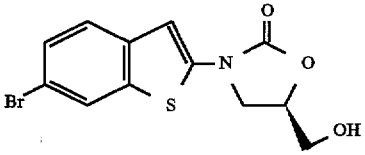

112 g (341 mmol) of the compound from Example V are dissolved in 1 l of THF, 10 mg of 1,10-phenanthroline hydrate are added and the mixture is cooled to –70° C. About 136 ml of a 2.5N n-butyllithium solution in hexane are now slowly added dropwise until the colour changes to red. 48.9 ml (350 mmol) of (R)-glycidyl butyrate are then added dropwise. The mixture is allowed to come to room temperature, saturated ammonium chloride solution is added, the organic phase is separated off and the aqueous phase is extracted twice with ethyl acetate. The combined organic phases are dried (Na$_2$SO$_4$) and concentrated. The residue is stirred in ether, filtered off with suction and dried.

Yield: 97.4 g (87%) Melting point: 246° C. $\alpha_D^{20}$=–54.2° (c=0.9, DMSO)

$^1$H-NMR (D$_6$-DMSO, TMS): 8.15 (d, J=2 Hz, 1H); 7.63 (d, J=7 Hz, 1H); 7.47 (dd, J=7 Hz, J=2 Hz, 1H); 6.8 (s, 1H);

5.28 (br, 1H); 4.7–4.95 (m, 1H); 4.19 (t, J=9.5 Hz, 1H); 3.92 (dd, J=9.5 Hz, 6.5 Hz, 1H); 3.55–3.80 (m, 2H).
The compounds listed in Table 1 are prepared analogously to the instructions of Example 4:
TABLE 1
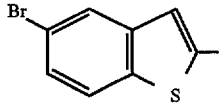
| Example No. | A | Analogously to the example sequence | Yield [% of theory] | Melting point [°C.] | $R_f$ mobile phase mixture (ratio) | $\alpha_D^{20}$ in DMSO (c =) |
|---|---|---|---|---|---|---|
| 5 | 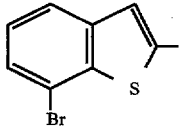 | I/II/1 | 51 | 223 | | −62.2° (1.0) |
| 6 | 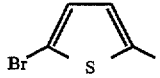 | I/II/1 | 65 | 130–136 | | −41.4° (1.6) |
| 7 | 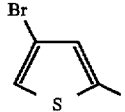 | I/II/1 | 70 | 109 | | −29.5° (1.1) |
| 8 | 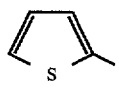 | I/II/1 | 60 | 156 | | −60.4° (0.8) |
| 9 |  | I/II/1 | 78 | 164 | | −58.7° (0.9) |
| 10 | 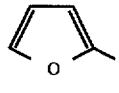 | I/II/1 | 79 | 132 | 0.16 II (6:4) | −51.4° (1.0) |
| 11 | 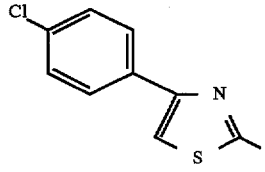 | I/II/1 | 80 | | | −31.4° (1.1) |
| 12 | 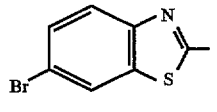 | IV/3 | 66 | | 0.07 II (10:1) | |
| 13 | 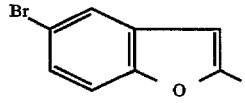 | III/2 | 14 | | 0.25 II (1:1) | |
| 14 | 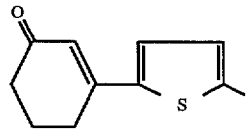 | I/V/6 | 80 | 169–170 | 0.23 I (1:1) | −53.2° (0.9) |
| 15 |  | I/V/6 | 43 | 178–180 | 0.34 I (100:5) | +0.8° (0.7) |

TABLE 1-continued

| Example No. | A | Analogously to the example sequence | Yield [% of theory] | Melting point [°C.] | R_f mobile phase mixture (ratio) | $\alpha_D^{20}$ in DMSO (c =) |
|---|---|---|---|---|---|---|
| 16 | 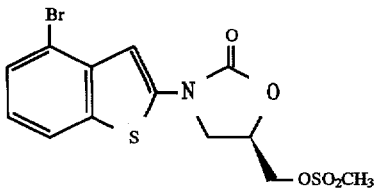 | I/V/6 | 73 | — | 0.25 II (1:1) | — |
| 17 | 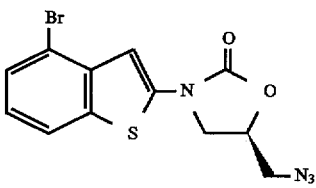 | I/V/6 | 42 | 186–187 | 0.12 II (1:1) | — |

EXAMPLE 18

(5R)-3-[4- Bromo-benzo[b ]thiophenyl ]-5-methanesulphonyloxymethyl-oxazolidin-2-one

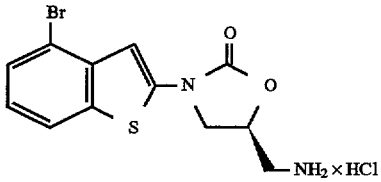

A solution of 22 g (67.3 mmol) of the compound from Example 1 and 15.5 ml (113 mmol) of triethylamine in 250 ml of methylene chloride is cooled to −10° C., and 8 ml (107 mmol) of methanesulphonyl chloride are slowly added. The mixture is subsequently stirred at −10° C. for 1 h and tipped onto ice-water. After the organic phase has been separated off, it is extracted successively with in each case once with dilute HCl, saturated NaHCO₃ and H₂O. The organic phase is dried with sodium sulphate and concentrated.

Yield: 25 g (92%)

¹H-NMR (D₆-DMSO,TMS): 7.92 (d, J=7.5 Hz, 1H); 7.58 (d, J=7.5 Hz, 1H); 7.18 (t, J=7.5 Hz, 1H); 6.72 (s, 1H); 5.11–5.28 (m, 1H); 4.57 (d, J=5 Hz, 2H); 4.36 (t, J=15 Hz, 1H); 4.02 (dd, J=15 Hz, J=6 Hz, 1H); 3.28 (s, 3H).

EXAMPLE 19

(5R)-3-[4-Bromo-benzo[b]thiophenyl]-5-azidomethyl-oxazolindin-2-one 25 g (62 mmol) of the compound from Example 18 are dissolved in 250 ml of DMF, and 4.4 g (67 mmol) of sodium azide are added. The reaction mixture thus obtained is stirred at 70° C. for 14 hours. It is allowed to cool to room temperature and is tipped onto 2 l of ice-water. The solid which has precipitated out is filtered off with suction, rinsed with water and petroleum ether and dried in air.

Yield: 20.3 g (93%) Melting point: 115° C. $\alpha_D^{20}$=−180.8° (DMSO c=0.5)

¹H-NMR (D₆-DMSO,TMS): 7.93 (d, J=7.5 Hz, 1H); 7.58 (d, J=7.5 Hz, 1H); 7.19 (t, J=7.5 Hz, 1H); 6.73 (s, 1H); 5.0–5.14 (m, 1H); 4.3 (t, J=10 Hz, 1H); 3.97 (dd, J=10 Hz, J=6 Hz, 1H); 3.8 (d, J=5 Hz, 2H). MS (DC): 353 (M⁺, 98%); 355 (M⁺2, 100%)

EXAMPLE 20

(5R)-3-[4-Bromo[b]thiophenyl]-5-aminomethyloxazolidin-2-one hydrochloride 20 g (57 mmol) of the compound from Example 19 are dissolved in 60 ml of ethylene glycol dimethyl ether and the solution is heated to 50° C. 8 ml (68 mmol) of trimethyl phosphite are slowly added dropwise (evolution of gas), and when the addition has ended the mixture is heated to 90° C. and subsequently stirred at 90° C. for 2 h. 10.7 ml (65 mmol) of 6N HCl are now added dropwise and the mixture is subsequently stirred again at 90° C. for 2 h. It is allowed to cool to room temperature and is concentrated and the residue is stirred with hot ethanol. The mixture is allowed to cool to room temperature and the precipitate is filtered off with suction. The precipitate is rinsed with a little ethanol and a large quantity of petroleum ether and dried under a high vacuum.

Yield: 15 g (73%) Melting point:>240° C.

¹H-NMR (D₆-DMSO,TMS): 7.92 (d, J=7.5 Hz, 1H); 7.56 (d, J=7.5 Hz, 1H); 7.19 (t, J=7.5 Hz, 1H); 6.68 (s, 1H);

5.05–5.22 (m, 1H); 4.38 (t, J=10 Hz, 1H); 4.04 (dd, J=10 Hz, J=6 Hz, 1H); 3.3 (d, J=6 Hz, 2H). $\alpha_D^{20}$ –60.7° (c=0.9, DMSO)

EXAMPLE 21

(5S)-3-[4-Bromo-benzo[b]thiophenyl]-5-acetyl-aminomethyl-oxazolidin-2-one

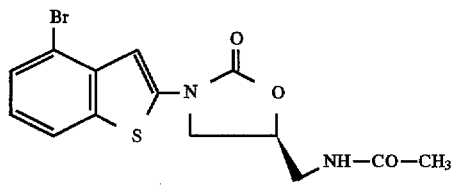

150 ml of methylene chloride and 13.9 ml (103 mmol) of triethylamine are added to 15 g (41 mmol) of the compound from Example 20. The reaction solution thus obtained is cooled to 0° C., while stirring, and 3.9 ml (57 mmol) of triethylamine are slowly added. The reaction solution thus obtained is cooled to 0° C., while stirring, and 3.9 ml (57 mmol) of acetyl chloride are slowly added. The mixture is subsequently stirred at 0° C. for 2 h and diluted with 200 ml of water and 150 ml of methylene chloride. The organic phase is separated off, the aqueous phase is rinsed once with methylene chloride and the combined organic phases are dried with sodium sulphate. The mixture is concentrated and the residue is stirred with 200 ml of ether and filtered off with suction.

Yield: 12.2 g (83% of theory) Melting point: 177° C.

$^1$H-NMR (D$_6$-DMSO, TMS): 8.28 (t, J=6.3 Hz, 1H); 7.92 (d, J=7.5 Hz, 1H); 7.58 (d, J=7.5 Hz, 1H); 7.19 (t, J=7.5 Hz, 1H); 6.68 (s, 1H); 4.83–4.96 (m, 1H); 4.29 (t, J=9.5 Hz, 1H); 3.9 (dd, J=9.5 Hz, J=6 Hz, 1H); 3.43–3.52 (m, 2H); 1.87 (s, 3H). MS (DCl): 370 (M$^+$–1, 40%)

The compounds listed in Table 2 are prepared analogously to the instructions of Examples 18–21:

TABLE 2

| Ex. No. | A | Yield [% of theory] | Melting point [°C.] | $\alpha_D^{20}$ in DMSO (c =) | Prepared from Example |
|---|---|---|---|---|---|
| 22 | 5-Br-benzo[b]thiophen-2-yl | 50 | 220 after decomposition | –39.2° (1.3) | 5 |
| 23 | 6-Br-benzo[b]thiophen-2-yl |  |  |  | 4 |
| 24 | 7-Br-benzo[b]thiophen-2-yl | 48 | 202 | +32.7° (0.7) | 6 |
| 25 | 5-Br-thiophen-2-yl | 75 | 165 | –12.2° (1.1) | 7 |
| 26 | 4-Br-thiophen-2-yl | 89 | 148 | –34.2° (1.4) | 8 |
| 27 | thiophen-2-yl | 70 | 117 | –26.7° (0.9) | 9 |
| 28 | thiophen-3-yl | 94 | 125 | –31.8° (1.5) | 10 |

TABLE 2-continued

Structure:
A—N(oxazolidin-2-one)—CH2—NH—C(=O)—CH3

| Ex. No. | A | Yield [% of theory] | Melting point [°C.] | α_D^20 in DMSO (c =) | Prepared from Example |
|---|---|---|---|---|---|
| 29 | C6H5-thiazolyl | 86 | 168 | −55.8° (0.6) | 3 |
| 30 | Br-thiazolyl | 83 | 165 | −14.6° C. (0.7) | 2 |
| 31 | Cl-phenyl-thiazolyl | 86 | — | — | 12 |
| 32 | Br-benzothiazolyl | 43 | 190–192 | | 13 |
| 33 | Br-benzofuranyl | 88 | 180 | −29.43 | 14 |
| 34 | cyclohexenone-thienyl | 75 | 182 | +39.4° (0.57) | 15 |
| 35 | H3C-phenyl-oxazolyl | 48 | 210 (decomposition) | −45.10 (1.0) | 16 |
| 36 | benzofuranyl | 85 | 109–110 | | 14 |

EXAMPLE 37

(5S)-3-[2-(5-Bromothiophenyl)]-5-acetylaminomethyl-oxazolidin-2-one

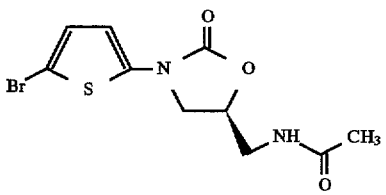

5.6 g (23.4 mmol) of the compound from Example 28 are dissolved in 65 ml of chloroform and 45 ml of acetonitrile and the solution is cooled to 0° C. A solution of 0.6 ml of bromine in 5 ml of chloroform is now slowly added dropwise and the mixture is allowed to come to room temperature overnight, while stirring. The mixture is concentrated, the residue is taken up in 200 ml of methylene chloride and the mixture is washed in each case once with dilute thiosulphate solution and water. The organic phase is dried with sodium sulphate and concentrated and the residue is chromatographed over silica gel with petroleum ether:ethyl acetate 1:1

Yield: 4.82 g (65%)

$^1$H-NMR (D$_6$-DMSO, TMS): 8.24 (t, J=6.5 Hz, 1H); 7.05 (d, J=5 Hz, 1H); 6.34 (d, J=5 Hz, 1H); 4.78–4.92 (m, 1H); 4.1 (t, J=8 Hz, 1H); 3.7 (dd, J=9 Hz, J=7 Hz, 1H); 3.4–3.48 (m, 2H); 1.8 (s, 3H).

EXAMPLE 38

(5S)-3-[2-(5-Iodthiophenyl)]-5-acetylaminomethyl-oxazolidin-2-one

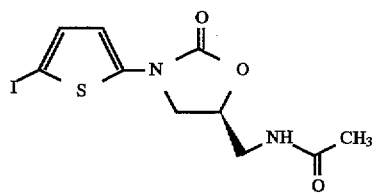

5 g (21 mmol) of the compound from Example 28 are dissolved in 60 ml of chloroform and 40 ml of acetonitrile, and 6.2 g (28 mmol) of silver trifluoroacetate are added. 5.6 g (22 mmol) of iodine are now added in portions and the mixture is subsequently stirred at room temperature for 48 h. The mixture is concentrated, the residue is taken up in methylene chloride and the mixture is washed in each case once with dilute sodium thiosulphate solution and water. The organic phase is dried with sodium sulphate and concentrated and the residue is chromatographed over silica gel with ethyl acetate:petroleum ether 3:7.

Yield: 5.7 g (75%) Melting point:>120° C. after decomposition $^1$H-NMR (D$_6$-DMSO, TMS): 8.25 (br, 1H); 7.14 (d, J=5 Hz, 1H); 6.26 (d, J=5 Hz, 1H); 4.7–4.9 (m, 1H); 4.08 (t, J=9 Hz, 1H); 3.68 (dd, J=9 Hz, J=6 Hz, 1H); 3.38–3.5 (m, 2H); 1.8 (s, 3H). MS (DCI): 367 (M$^+$+1, 100%).

EXAMPLE 39

(5S)-3-{2[5-(4-Methylphenyl)]thiophenyl}-5-acetyl-aminomethyl-oxazolidin-2-one

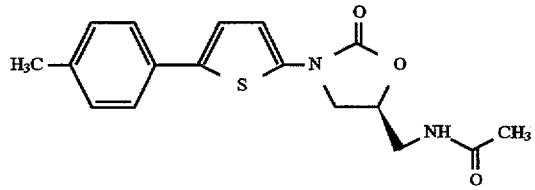

510 mg (1.6 mmol) of the compound from Example 25 and 286 mg (2.1 mmol) of 4-methylphenylboronic acid are dissolved in 10 ml of toluene, and 55 mg (0.048 mmol) of Pd(P(C$_6$H$_5$)$_3$)$_4$ are added. The solution thus obtained is boiled under reflux for 1 hour and 2.2 ml of 2M Na$_2$CO$_3$ are then added. The mixture is now boiled under reflux for 16 h, cooled to room temperature and concentrated and the residue is chromatographed over silica gel (petroleum ether/ethyl acetate 2:8).

Yield: 240 mg (45%) Melting point: 215° C. with decomposition $\alpha_D^{20}$+6.4° (DMSO, c=0.96) MS (DCI): 331 (M$^+$+1, 100%)

$^1$H-NMR (DCI): 8.27 (t, J=7 Hz, 1H); 7.48 (d, J=8 Hz, 2H); 7.22 (d, J=5 Hz, 1H); 7.18 (d, J=8 Hz, 2H); 6.5 (d, J=5 Hz, 1H); 4.77–4.90 (m, 1H); 4.14 (t, J=9 Hz, 1H); 3.74 (dd, J=9 Hz, J=6 Hz, 1H); 3.4–3.5 (m, 2H); 2.3 (s, 3H); 1.83 (s, 3H).

EXAMPLE 40

(5S)-3-{2[5-(2-Formylphenyl)]thiophenyl}-5-acetylamino-methyl-oxazolidin-2-one

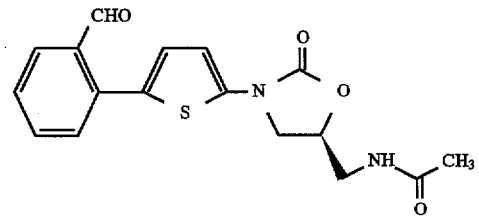

510 mg (1.6 mmol) of the compound from Example 25 and 315 mg (2.1 mmol) of 2-formyl-phenylboronic acid (J. Org. Chem. 57 (3), 1992, pages 1015–18) are dissolved in 10 ml of THF, 55 mg (0.048 mmol) of Pd(P(C$_6$H$_5$)$_3$)$_4$ are added and the mixture is boiled under reflux for 1 h. 2.2 ml of 2M Na$_2$CO$_3$ solution are added, the mixture is boiled under reflux for 16 h, cooled to room temperature and concentrated and the residue is chromatographed over silica gel (petroleum ether/ethyl acetate 4:6).

Yield: 434 mg (79%) Melting point: 151° C. $\alpha_D^{20}$=–6.3° (DMSO, c=0.98) MS (DCI): 345 (M$^+$+1, 30%)

$^1$H-NMR (D$_6$-DMSO, TMS): 10.1 (s, 1H); 8.29 (t, J=7 Hz, 1H); 7.88–7.93 (m, 1H); 7.7–7.78 (m, 1H); 7.5–7.63 (m, 1H); 7.08 (d, J=4 Hz, 1H); 6.67 (d, J=4 Hz, 1H); 4.7–4.95 (m, 1H); 4.19 (t, J=9 Hz, 1H); 3.8 (dd, J=9 Hz, J=6 Hz, 1H); 3.48 (t, J=6 Hz, 2H); 1.87 (s, 3H).

EXAMPLE 41

(5S)-3-[5-(2-Formyl-3-thienyl)-2-thiazolyl]-5-acetylaminomethyloxazolidin-5-one

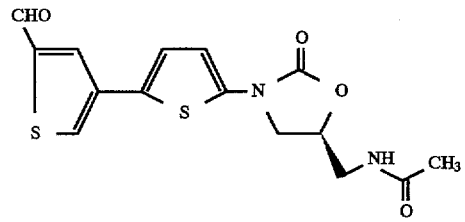

510 mg (1.6 mmol) of the compound from Example 25 and 320 mg (2.1 mmol) of 4-(2-formyl)thiopheneboronic acid are dissolved in 10 ml of THF, 55 mg (0.048 mmol) of Pd(PPh$_3$)$_4$ are added and the mixture is boiled under reflux for 1 h. 2.2 ml of 2M Na$_2$CO$_3$ solution are added, the mixture is boiled under reflux for 16 h, cooled to room temperature and filtered and the residue is washed with water, THF and ether and dried.

Yield: 270 mg (48%) $\alpha_D^{20}$=–4.3° (DMSO, c=1.0) Melting point: >205° C. with decomposition MS (DCI): 351 (M$^+$+1, 19%)

$^1$H-NMR (D$_6$-DMSO, TMS): 9.95 (s, 1H); 8.34 (s, 1H); 8.28 (t, J=7 Hz, 1H); 8.17 (s, 1H); 7.30 (d, J=4 Hz, 1H); 6.53 (d, J=4 Hz, 1H); 4.7–4.95 (m, 1H); 4.15 (t, J=9 Hz, 1H); 3.77 (dd, J=9 Hz, J=6 Hz, 1H); 3.48 (t, J=6 Hz, 2H); 1.85 (s, 3H).

The compounds listed in Table 3 are prepared analogously to the instructions of Examples 39–41:

TABLE 3

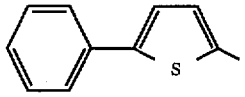

| Ex. No. | A | Prepared from Example No. | Yield (% of theory) | Melting point (°C.) | $\alpha_D^{20}$ (DMSO) (c =) |
|---|---|---|---|---|---|
| 42 | 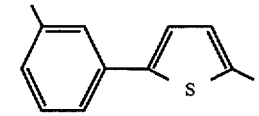 | 25 | 43 | 191 | +5.3° (0.9) |
| 43 | 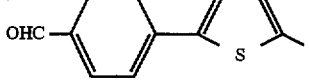 | 25 | 84 | >170 with decomposition | +7.2° (0.9) |
| 44 |  | 25 | 66 | 229 with decomposition | −26° (1) |
| 45 | 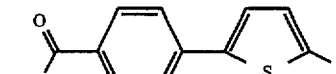 | 25 | 7 | >230 with decomposition | — |
| 46 | 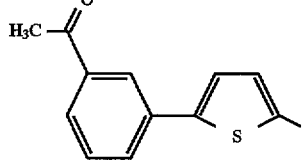 | 25 | 47 | 201 with decomposition | +18.8° (1) |
| 47 | 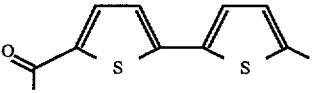 | 25 | 70 | 217 with decomposition | +2.8° (1.1) |
| 48 | 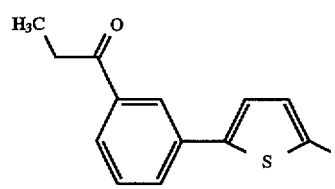 | 25 | 40 | 211 with decomposition | +14.7° (1) |
| 49 | 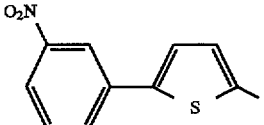 | 25 | 67 | 211 with decomposition | +7.1° (0.7) |
| 50 | 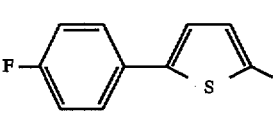 | 25 | 30 | >270 | +9.7° (1) |
| 51 |  | 25 | 77 | 222 after decomposition | +5.7° (1) |

TABLE 3-continued

| Ex. No. | A | Prepared from Example No. | Yield (% of theory) | Melting point (°C.) | $\alpha_D^{20}$ (DMSO) (c =) |
|---|---|---|---|---|---|
| 52 | 4-Cl-phenyl-thiophene | 25 | 49 | 241 | +12.3° (0.9) |
| 53 | 4-F-3-Cl-phenyl-thiophene | 25 | 47 | 228 | +6.2° (1.0) |
| 54 | phenyl-CH=CH-thiophene | 25 | 69 | 201 | +32.2° (0.9) |
| 55 | 4-CH₃O-phenyl-thiophene | 25 | 55 | 230 with decomposition | +75° (1.0) |
| 56 | 3-(HCl·H₂N)-phenyl-thiophene | 25 | 51 | 208 | +10.1° (1.1) |
| 57 | phenyl-CH=CH-thiophene (isomer) | 26 | 45 | 203 | −47.7° (1) |
| 58 | 4-CH₃-phenyl-CH=CH-thiophene | 26 | 64 | 217 | −48.7° (1.2) |
| 59 | 3-OHC-phenyl-CH=CH-thiophene | 26 | 86 | 155–163 with decomposition | −39.8° (1.1) |
| 60 | 4-OHC-phenyl-CH=CH-thiophene | 26 | 53 | 175 | −47.6° (0.9) |
| 61 | 4-(H₃C-CO)-phenyl-CH=CH-thiophene | 26 | 45 | 168 | −44.5° (0.9) |

TABLE 3-continued
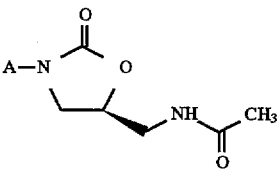
| Ex. No. | A | Prepared from Example No. | Yield (% of theory) | Melting point (°C.) | $\alpha_D^{20}$ (DMSO) (c =) |
|---|---|---|---|---|---|
| 62 | 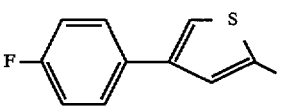 | 26 | 59 | 209 with decomposition | −55.2° (0.9) |
| 63 | 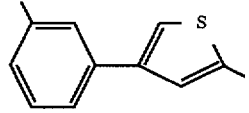 | 26 | 70 | 178 with decomposition | −47.3° (1.1) |
| 64 | 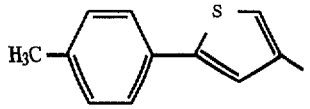 | 26 | 18 | 194 with decomposition | |
| 65 | 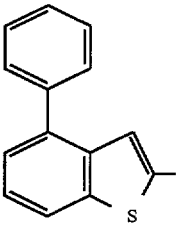 | 26 | 62 | 140 | −21.37° (0.7) |
| 66 | 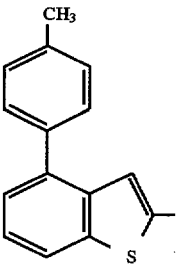 | 21 | 57 | 188 | |
| 67 | 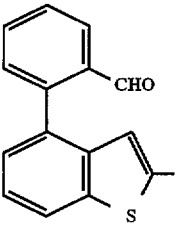 | 21 | 58 | 189 | −66° (0.9) |
| 68 |  | 21 | 53 | 107 | −63.5° (1.0) |

TABLE 3-continued

| Ex. No. | A | Prepared from Example No. | Yield (% of theory) | Melting point (°C.) | $\alpha_D^{20}$ (DMSO) (c =) |
|---|---|---|---|---|---|
| 69 | 3-CHO-phenyl-benzothiophene | 21 | 63 | 116 | −81.4° (0.7) |
| 70 | 4-CHO-phenyl-benzothiophene | 21 | 43 | 118 | −75.5° (0.6) |
| 71 | 4-acetyl-phenyl-benzothiophene | 21 | 44 | 231 | −74.4° (0.9) |
| 72 | 4-F-phenyl-benzothiophene | 21 | 63 | 198 | −63.5° (1.0) |
| 73 | 3-NH₂-phenyl-benzothiophene | 21 | 47 | 109 | −62.8° (0.8) |

TABLE 3-continued

A—N‑[oxazolidinone core]‑CH₂NHC(O)CH₃

| Ex. No. | A | Prepared from Example No. | Yield (% of theory) | Melting point (°C.) | α_D²⁰ (DMSO) (c =) |
|---|---|---|---|---|---|
| 74 | 3-acetylphenyl-benzothiophen-2-methyl | 21 | 27 | 97 | −64.2° (0.7) |
| 75 | 2-(2-isopropylthiazol-4-yl)phenyl-CHO | 26 | 85 | 144 | |
| 76 | 2-acetyl-5-(2-isopropylthiazol-4-yl)thiophene | 25 | 51 | 195 with decomposition | −60° (0.7) |
| 77 | 2-isopropyl-4-(1-phenylvinyl)thiazole | 30 | 76 | 165 | −0.9 (0.7) |
| 78 | 4-acetylphenyl-(2-isopropylthiazol-4-yl) | 30 | 76 | 230 | −68.6 (0.6) |
| 79 | 4-formylphenyl-(2-isopropylthiazol-4-yl) | 30 | 98 | 210 | −76.6 (0.6) |
| 80 | 5-formyl-2-(2-isopropylthiazol-4-yl)thiophene | 30 | 81 | 205 | −78.4° (0.6) |
| 81 | 3-acetylphenyl-(2-methylbenzothiophen-5-yl) | 22 | 49 | 198 with decomposition | |
| 82 | 4-fluorophenyl-(2-methylbenzothiophen-5-yl) | 22 | 60 | 226 with decomposition | −46° (0.8) |

TABLE 3-continued
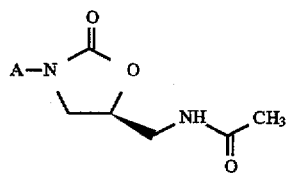
| Ex. No. | A | Prepared from Example No. | Yield (% of theory) | Melting point (°C.) | $\alpha_D^{20}$ (DMSO) (c =) |
|---|---|---|---|---|---|
| 83 | | 30 | 69 | | |
| 84 | | 30 | 15 | | |
| 85 | | 22 | 44 | 225 with decomposition | |
| 86 | | 22 | 72 | 224 with decomposition | −30.2° (0.8) |
| 87 | | 22 | 72 | 218 with decomposition | −29.8° (0.8) |
| 88 | | 22 | 78 | 244 with decomposition | −40.1° (0.7) |
| 89 | | 21 | 68 | 70 with decomposition | −76.3° (0.9) |

TABLE 3-continued
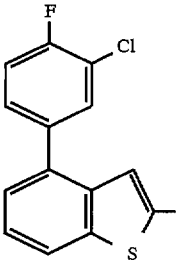
| Ex. No. | A | Prepared from Example No. | Yield (% of theory) | Melting point (°C.) | $\alpha_D^{20}$ (DMSO) (c =) |
|---|---|---|---|---|---|
| 90 | 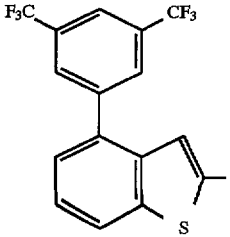 | 21 | 65 | 193 | −52.3° (0.7) |
| 91 | 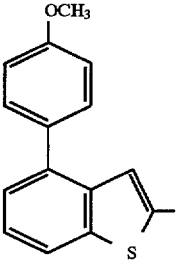 | 21 | 60 | 193 | −57.4° (1.0) |
| 92 | 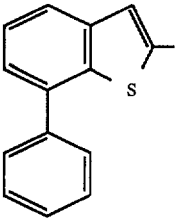 | 21 | 71 | 174 | −57.7° (1.0) |
| 93 | 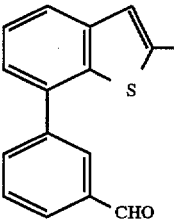 | 24 | 83 | 193 | |
| 94 |  | 24 | 54 | 94 | |

TABLE 3-continued

[Structure: A—N in oxazolidinone ring with CH₂NHC(O)CH₃ substituent]

| Ex. No. | A | Prepared from Example No. | Yield (% of theory) | Melting point (°C.) | $\alpha_D^{20}$ (DMSO) (c =) |
|---|---|---|---|---|---|
| 95 | 4-OHC-C₆H₄-benzothiophen-5-yl | 22 | 67 | 211 | −46.2° (0.7) |
| 96 | phenyl-benzothiophen-5-yl | 22 | 73 | 220 | |
| 97 | 3-OHC-C₆H₄-benzothiophen-5-yl | 22 | 75 | 214 with decomposition | −40.9° (0.7) |
| 98 | 5-acetyl-thiophen-2-yl-benzothiophen-5-yl | 22 | 9 | 235 with decomposition | |
| 99 | 7-(4-CHO-phenyl)-benzothiophen-2-yl | 24 | 47 | 100 with decomposition | |
| 100 | 7-(4-F-phenyl)-benzothiophen-2-yl | 24 | 42 | 194 | |

EXAMPLE 101

(5S)-3-(2-[5-(4-hydroxymethyl)phenyl]thiophenyl)-5-acetylamino-methyl-oxazolidin-2-one

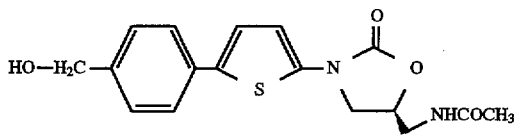

100 mg (0.29 mmol) of the compound from Example 44 are dissolved in 3.2 ml of methanol, the solution is cooled to 0° C. and 6 mg (0.15 mmol) of NaBH$_4$ are added; the mixture is kept at 0° C. for 3 h, 5 ml of water are added, the mixture is subsequently stirred at room temperature for 1 h and the precipitate is filtered off with suction and dried.

Yield: 69 mg (69%) Melting point: 224° C. after decomposition MS (FAB): 346 [M$^+$, 100%], 347 [M$^+$+1, 80%]

$^1$H-NMR (D$_6$-DMSO, TMS): 8.28 (t, J=7 Hz, 1H); 7.55 (d, J=9 Hz, 2H); 7.3 (d, J=7 Hz, 2H); 7.28 (d, J=5 Hz, 1H); 6.51 (d, J=5 Hz, 1H); 5.19 (t, J=6 Hz, 1H); 4.78–4.92 (m, 1H); 4.47 (d, J=6 Hz, 1H); 4.13 (t, J=9 Hz, 1H); 3.75 (dd, J=9 Hz, J=6 Hz, 1H); 3.43 (t, J=6 Hz, 2H); 1.89 (s, 3H).

The compounds listed in Table 4 are prepared analogously to the instructions of Example 101:

overnight, 5 ml of ethanol are added, the mixture is boiled under reflux for 10 min, 10 ml of saturated NaHCO$_3$ solution are added and the brown precipitate is filtered off with suction, rinsed with water and with ether and dried in vacuo at 50° C.

Yield: 114 mg (27%) Melting point: 258° C. with decomposition $^1$H-NMR (D$_6$-DMSO, TMS): 12.95 (br, 1H); 8.28 (t, J=7 Hz, 1H); 7.95 (d, J=8 Hz, 2H); 7.72 (d, J=8 Hz, 2H); 7.5 (d, J=5 Hz, 1H); 6.58 (d, J=5 Hz, 1H); 4.7–4.95 (m, 1H); 4.17 (t, J=9 Hz, 1H); 3.77 (dd, J=9 Hz, J=6 Hz, 1H); 3.43 (t, J=6 Hz, 2H); 1.83 (s, 3H).

TABLE 4

| Ex. No. | A | Prepared from Example No. | Yield (% of theory) | Melting point (°C.) |
| --- | --- | --- | --- | --- |
| 102 | HOH$_2$C–[phenyl]–[thiophene]– | 44 | 52 | 190 with decomposition |
| 103 | H$_3$C–CH(OH)–[phenyl]–[benzothiophene]– | 85 | 48 | 227 with decomposition |

EXAMPLE 104

(5S)-3-(2-[5-(4-carboxyphenyl)thiophenyl)-5-acetyl-aminomethyl-oxazolidin-2-one

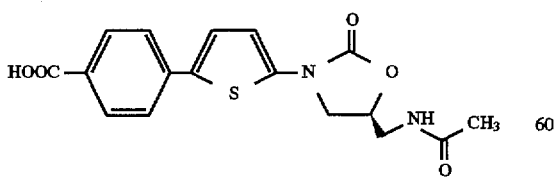

400 mg (1.16 mmol) of the compound from Example 44 are dissolved in 40 ml of acetone and 5 ml of water, and 211 mg (1.76 mmol) of MgSO$_4$ and 190 mg (1.2 mmol) of KMnO$_4$ are added. The mixture is stirred at room temperature

EXAMPLE 105

4-(Benzo[b]furan-2-yl)-5-amidomethyloxazolidin-2-one

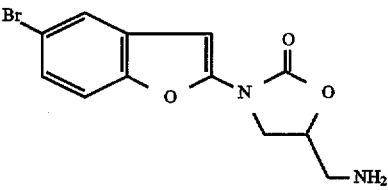

20 g (59.3 mmol) of the corresponding azide and 500 mg of platinum(IV) oxide in 500 ml of methanol are stirred at room temperature under hydrogen (1 atmosphere) for 3 h. The catalyst is filtered off, the solvent is stripped off and the residue is dried under a high vacuum.

Yield: 19.0 g (quantitative)

$^1$H-NMR (D$_6$-DMSO, TMS): 7.78 (d, J=2 Hz, 1H); 7.50 (d, J=8 Hz, 1H); 7.35 (dd, J=8 Hz, J=2Hz, 1H); 4.65–4.82 (m, 1H), 4.22 (t, J=9 Hz, 1H); 4.03 (dd, J=9 Hz, J=5 Hz, 1H), 3.20–3.55 (bs, 2H), 2.70–2.95 (m, 2H).

The compounds listed in Table 5 are prepared analogously to the instructions of Example 4:

TABLE 5

A—N-C(=O)-O-CH<sub>2</sub>-CH(—)-CH<sub>2</sub>OH (structure as drawn)

| Ex. No. | A | Analogously to example sequence | Yield [% of theory] | melting point [°C.] | Rf mobile point phase mixture (ratio) | α$_D^{20}$ in DMSO (c =) |
|---|---|---|---|---|---|---|
| 106 | O$_2$N-benzothiophen-2-yl | I/V/6 | 94 | 217 |  | −70.4° (1.0) |
| 107 | F-benzothiophen-2-yl | I/V/6 | 80 | 290 with decomposition | V 0.72 (1/1) |  |
| 108 | CH$_3$-benzothiophen-2-yl | I/V/6 | 93 | 239 | I 0.19 (100/1) | −61.8° (1.0) |
| 109 | F-benzothiophen-2-yl (isomer) | I/V/6 | 40 | 202 | 0.1 V (1/1) |  |
| 110 | Cl-benzothiophen-2-yl | I/V/6 | 98 |  | 0.5 I (100/1) |  |
| 111 | N≡C-benzothiophen-2-yl | I/V/6 | 98 |  | 0.18 II (2:1) |  |
| 112 | 2-phenyl-thiazol-4-yl | I/V/6 | 79 |  | 0.1 II (1:1) |  |

The compounds listed in Table 6 are prepared analogously to the instructions of Examples 18 to 21:

TABLE 6

A—N(C=O)—O—CH(NH—CO—CH₃)—CH₂— (oxazolidinone with NHCOCH₃ substituent)

| Ex. No. | A | Yield [% of theory] | Melting point [°C.] | $\alpha_D^{20}$ in DMSO (c =) | Prepared from example |
|---|---|---|---|---|---|
| 113 | 5-F-benzothiophen-2-yl | 75 | 198 | −32.6° (1.2) | 107 |
| 114 | 5-CH₃-benzothiophen-2-yl | 40 | 218 | −40.9° (1.0) | 108 |
| 115 | 5-NC-benzothiophen-2-yl |  | 217 |  | 111 |
| 116 | 6-F-benzothiophen-2-yl |  |  |  | 109 |
| 117 | 6-Cl-benzothiophen-2-yl |  |  |  | 110 |
| 118 | 2-phenyl-thiazol-4-yl (4-methyl) | 63 |  |  | 112 |

The compounds listed in Table 7 are prepared analogously to the instructions of Examples 39 to 41:

TABLE 7

A—N(C=O)—O—CH(NH—CO—CH₃)—CH₂—

| Ex. No. | A | Prepared from Example No. | Yield [% of theory] | Melting point [°C.] |
|---|---|---|---|---|
| 119 | 4-(4-HOOC-phenyl)-benzothiophen-2-yl | 22 | 24 | >275° with decomposition |

TABLE 7-continued

[Structure: A—N—C(=O)—O—CH—CH2 ring with —NH—CO—CH3 substituent]

| Ex. No. | A | Prepared from Example No. | Yield [% of theory] | Melting point [°C.] |
|---|---|---|---|---|
| 120 | pyridyl-thiophene | 26 | 53 | 229° with decomposition |
| 121 | 4-formylphenyl-benzo[b]thiophene | 23 | 44 | 240° with decomposition |
| 122 | 4-acetylphenyl-benzo[b]thiophene | 23 | 43 | 261° with decomposition |
| 123 | phenyl-benzo[b]thiophene | 23 | 55 | 237° with decomposition |
| 124 | pyridyl-thiophene | 25 | 50 | 227° with decomposition |

EXAMPLE 125

(5R)-3-[4-carboxymethyl-benzo[b]-thiophenyl]-5-acetyl-aminomethyl-oxazolidin-2-one

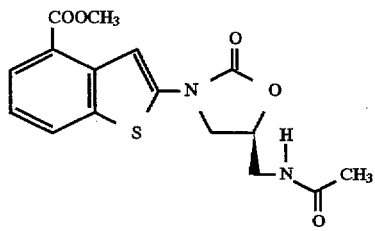

100 mg (0.27 mmol) of the compound from Example 21 are dissolved in 4 ml of methanol and 2 ml of THF, 2 ml of triethylamine and 31 mg (0.027 mmol) of Pd(PPh3)2Cl2 are added and the mixture is boiled under reflux for 48 h. It is concentrated and the residue is chromatographed over silica gel with methylene chloride/methanol (100/0.5).

Yield: 55 mg (58%) Rf: 0.36 (I; 100/5) Melting point: 193° C. with decomposition $^1$H-NMR (D$_6$-DMSO, TMS): δ=8.28 (t, J=6.5 Hz, 1H); 8.19 (d, J=7.5 Hz, 1H); 8.02 (d, J=7.5 Hz, 1H); 7.4 (s, 1H); 7.36 (t, J=7.5 Hz, 1H); 4.83–4.96 (m, 1H); 4.30 (t, J=9.5 Hz, 1H); 3.9 (dd, J=9.5 Hz, J=6 Hz, 1H); 3.88 (s, 3H); 3.43–3.52 (m, 2H); 1.88 (s, 3H) MSE: 348 (M$^+$, 100%)

The compounds listed in Table 8 are prepared analogously to the instructions of Example 125:

TABLE 8

A—N structure with acetyl oxazolidinone and NHCOCH3 substituent

| Ex. No. | A | Prepared from Example No. | Yield (% of theory) | Melting point (°C.) |
|---|---|---|---|---|
| 126 | 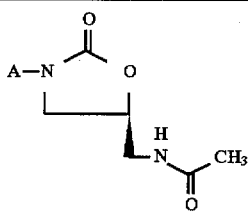 CH₃OOC-benzothiophene | 23 | 20 | 220° |
| 127 | CH₃OOC-benzothiophene (isomer) | 22 | 19 | 166° |
| 128* | benzothiophene | 23 | 20 | 186° |

*Compound No. 128 was formed as a by-product of the preparation of compound No. 126.

TABLE 9

N-phenyl-pyrrolyl-cyclopentyl-oxazolidinone structure with R₁

| Ex. No. | $R_1$ | Prepared in analogy to Example No. | Yield (% of theory) | Melting point (°C./$R_f$)* |
|---|---|---|---|---|
| 129 | —OH | 4 | 36 | 220° |
| 130 | —NH—CO—CH₃ | 21 | 56 | 0,170/196 |

We claim:

1. A heteroaryl-oxazolidinone of the formula

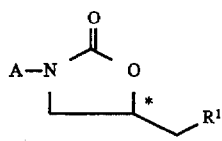

(I)

in which

R¹ represents azido; hydroxy; or a group of the formula —OR², —O—SO₂—R³ or —NR⁴R⁵, wherein R² denotes straight-chain or branched acyl having up to 8 carbon atoms or a hydroxyl-protective group, R³ denotes straight-chain or branched alkyl having up to 4 carbon atoms or optionally substituted wherein the substituent is a straight-chain or branched alkyl having up to 4 carbon atoms, R⁴ and R⁵ are identical or different and denote hydrogen, or an amino-protective group, or R⁴ and R⁵ denotes a group of the formula —CO—R⁶, wherein R⁶ denotes cycloalkyl having 3 to 6 carbon atoms, straight-chain or branched alkyl having up to 8 carbon atoms, phenyl or hydrogen, A represents a 5-membered aromatic heterocyclic radical, which has up to 3-heteroatoms selected from the group consisting of S, N or O, is directly bonded by a carbon atom and can additionally have a fused-on benzene or naphthyl ring, wherein the heterocyclic cyclic radicals are substituted in each case up to 3 times in an identical or different manner by carboxyl; halogen; cyano; mercapto; formyl; trifluoromethyl; nitro; straight-chain or branched C₁-C₆-alkoxy, straight-chain or branched C₁-C₆-alkoxycarbonyl; straight-chain or branched C₁-C₆-alkylthio; straight-chain or branched C₁-C₆-acyl; or optionally substituted straight-chain or branched alkyl having up to 6 carbon atoms, wherein the substituents are hydroxyl, straight-chain or branched C₁-C₅-alkoxy, C₁-C₅-acyl, or a group of the formula —NR⁷R⁸, wherein R⁷ and R⁸ are identical or different and denote hydrogen, straight-chain or branched alkyl having up to 4 carbon atoms or phenyl, or R⁷ and R⁸ together with the nitrogen atom form an optionally substituted 5- to 6-membered saturated heterocyclic radical which optionally has a further hetero atom selected from the group consisting of N, S or O wherein the substituents are straight-chain or branched C₁-C₂-alkyl or straight-chain or branched C₁-C₃-acyl, and/or the heterocyclic radicals as defined in A are substituted by a group of the formula —NR⁷'R⁸', wherein R⁷' and R⁸' are identical or different and have the above-mentioned meaning of R⁷ and R⁸ and are identical to or different from these, and/or the heterocyclic cyclic radicals as defined in A are substituted by optionally mono or disubstituted ($C_2$–$C_8$)-alkenylphenyl, optionally mono or disubstituted phenyl or by a 5- or 6-membered saturated or unsaturated mono or disubstituted heterocyclic radical having up to 3 hetero atoms selected from the group consisting of S, N or O, wherein the optional substituents are carboxyl; halogen; cyano; mercapto; formyl; trifluoromethyl; nitro; phenyl; straight-chain or branched $C_1$–$C_6$-alkoxy; straight-chain or branched $C_1$–$C_6$-alkoxycarbonyl; straight-chain or branched $C_1$–$C_6$-alkylthio, straight-chain or branched $C_1$–$C_6$-acyl; straight-chain or branched $C_1$–$C_6$-alkyl wherein said alkyl is optionally substituted by hydroxyl, straight-chain or branched $C_1$–$C_5$-alkoxy, straight-chain or branched $C_1$–$C_5$-acyl or a group of the formula —$NR^{18}R^{19}$, $R^{18}$ and $R^{19}$ have the abovementioned meaning of $R^7$ and $R^8$ and are identical to or different from these; or substituted once by a group of the formula —CO—$NR^9R^{10}$, —$NR^{11}R^{12}$, —$NR^{13}$—$S(O)_2$—$R^{14}$, $R^{15}R^{16}N$—$SO_2$— or $R^{17}$—$S(O)_a$— wherein a denotes a number 0, 1 or 2, $R^9$, $R^{10}$, $R^{13}$, $R^{15}$ and $R^{16}$ are identical or different and denote hydrogen, straight-chain or branched alkyl having up to 6 carbon atoms or phenyl, $R^{11}$ and $R^{12}$ are identical or different and have the abovementioned meaning of $R^7$ and $R^8$ and are identical or different from these, $R^{14}$ and $R^{17}$ are identical or different and have the abovementioned meaning of $R^3$ and are identical to or different from this, and/or the heterocyclic cyclic radicals are substituted by a radical of the formula

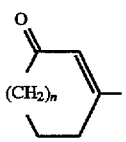

wherein n denotes the number 0, 1 or 2, or a salt or S-oxide thereof.

2. A heteroaryl-oxazolidinone according to claim 1, in which $R^1$ represents azido; hydroxyl; or a group of the formula —$OR^2$, —$OSO_2^{R3}$ or —$NR^4R^5$, wherein $R^2$ denotes straight-chain or branched acyl having up to 6 carbon atoms or benzyl, $R^3$ denotes straight-chain or branched alkyl having up to 3 carbon atoms, phenyl or tolyl, $R^4$ and $R^5$ are identical or different and denote hydrogen or straight-chain tert-butoxycarbonyl or benzyloxycarbonyl, or $R^4$ or $R^5$ denotes a group of the formula —CO—$R^6$, wherein $R^6$ denotes cyclopropyl, cyclobutyl, cyclopentyl, cyclohexyl or straight-chain or branched alkyl having up to 6 carbon atoms, phenyl or hydrogen, A represents a heterocyclic radical selected from the group consisting of pyrrolyl; imidazolyl; furyl; thienyl; thiazolyl; oxazolyl; isothiazolyl; furazanyl; indolyl; benzo[b]thienyl; naphtho[2,3-b]thienyl; benzo[b]thiazolyl; benzo[b]imidazolyl; or benzo[b]furanyl wherein said heterocylic radicals are substituted in each case up to 3 times in an identical or different manner by carboxy; fluorine; chlorine; bromine; iodine; cyano; mercapto; trifluoromethyl; formyl; nitro; straight-chain or branched $C_1$–$C_4$-alkoxy; alkoxycarbonyl; straight-chain or branched $C_1$–$C_4$-alkylthio; straight-chain or branched $C_1$–$C_4$-acyl; or optionally substituted straight-chain or branched $C_1$–$C_4$-alkyl wherein the substituents are hydroxyl, straight-chain or branched alkoxy or acyl having up to 4 carbon atoms, or a group of the formula —$NR^7R^8$, wherein $R^7$ and $R^8$ are identical or different and denote hydrogen, straight-chain or branched alkyl having up to 3 carbon atoms or phenyl, or $R^7$ and $R^8$ together with the nitrogen atom form a morpholinyl, pyrrolidinyl, piperazinyl or piperidyl ring which are optionally substituted, including via the free N function, by substituents selected from the group consisting of methyl, ethyl or acetyl, and/or the heterocyclic radicals as defined in A are substituted by a group of the formula —$NR^7R^{8'}$, wherein $R^7$ and $R^8$ have the abovementioned meaning of $R^7$ and $R^8$ and are identical to or different from these, and/or the heterocyclic radicals as defined in A are substituted by ($C_2$–$C_4$)-alkenylphenyl, phenyl, optionally substituted pyridyl or optionally substituted thienyl, wherein the substituents are carboxyl; fluorine; chlorine; bromine; iodine; cyano; mercapto; trifluoromethyl; formyl; nitro; phenyl; straight-chain or branched $C_1$–$C_4$-alkoxy; straight-chain or branched $C_1$–$C_4$-alkoxycarbonyl; straight-chain or branched $C_1$–$C_4$-alkylthio; straight-chain or branched $C_1$–$C_4$-acyl or optionally substituted straight-chain or branched $C_1$–$C_4$-alkyl wherein the substituents are straight-chain or branched $C_1$–$C_4$-alkoxy; straight-chain or branched $C_1$–$C_4$-acyl or a group of the formula —$NR^{18}R^{19}$, wherein $R^{18}$ and $R^{19}$ have the abovementioned meaning of $R^7$ and $R^8$ and are identical to or different from these, or are substituted by a group of the formula —CO—$NR^9R^{10}$, —$NR^{11}R^{12}$, —$NR^{13}$, —$SO_2$—$R^{14}$, $R^{15}R^{16}N$—$SO_2$— or $R^{17}$—$S(O)_a$—, wherein a denotes the number 0, 1 or 2, $R^9$, $R^{10}$, $R^{13}$, $R^{15}$ and $R^{16}$ are identical or different and denote hydrogen, straight-chain or branched alkyl having up to 4 carbon atoms or phenyl, $R^{11}$ and $R^{12}$ are identical or different and have the abovementioned meaning of $R^7$ and $R^8$ and are identical to or different from these, $R^{14}$ and $R^{17}$ are identical or different and have the abovementioned meaning of $R^3$ and are identical to or different from this, and/or the heterocyclic radicals as defined in A are further optionally substituted by a radical of the formula

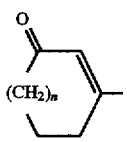

wherein n denotes the number 0, 1 or 2, or a salt or a S-oxide thereof.

3. A heteroaryl-oxazolidinone according to claim 1, in which $R^1$ represents azido; hydroxyl; or a group of the formula —$OR^2$, —$OSO_2{}^{R3}$ or —$NR^4R^5$, wherein $R^2$ denotes straight-chain or branched acyl having up to 6 carbon atoms, $R^3$ denotes methyl, ethyl, phenyl or tolyl, $R^4$ and $R^5$ are hydrogen, or $R^4$ or $R^5$ denotes a group of the formula —CO—$R^6$, wherein $R^6$ denotes cyclopropyl, cyclopentyl, cyclohexyl or straight-chain or branched alkyl having up to 4 carbon atoms, hydrogen or phenyl, A represents a heterocyclic radical selected from the group consisting of pyrrolyl; imidazolyl; furyl, thienyl; thiazolyl; isothiazolyl; isoxazolyl; furanzanyl; oxazolyl; indolyl; benzo[b]thienyl; benzo[b]imidazolyl; benzo[b]furanyl; benzo[b]thiazolyl wherein said heterocyclic radicals are substituted in each case up to twice in an identical or different manner by carboxyl; fluorine; chlorine; bromine; iodine; cyano; formyl; trifluoromethyl; nitro; straight-chain or branched $C_1$-$C_4$-alkoxy; straight-chain or branched $C_1$-$C_4$-alkoxycarbonyl; straight-chain branched $C_1$-$C_4$-acyl; or optionally substituted straight-chain or branched $C_1$-$C_4$-alkyl wherein the substituents are hydroxyl; straight-chain or branched $C_1$-$C_4$-alkoxy; straight-chain or branched $C_1$-$C_4$-acyl; or by a group of the formula —$NR^7R^8$, wherein $R^7$ and $R^8$ are identical or different and denote hydrogen or methyl, or together $R^7$ and $R^8$ with the nitrogen atom form a morpholinyl, pyrrolidinyl, piperazinyl or piperidyl ring, which are optionally substituted, including via the free N function, by methyl, ethyl or acetyl, and/or heterocyclic radicals as defined in A are substituted by a group of the formula —$NR^{7'}R^{8'}$, wherein $R^{7'}$ and $R^{8'}$ have the abovementioned meaning of $R^7$ and $R^8$ and are identical to or different from these, and/or the heterocyclic radicals as defined in A are substituted by 2-phenylvinyl, phenyl, optionally substituted pyridinyl or optionally substituted thienyl, wherein the substituents are carboxyl; fluorine; chlorine; bromine; iodine; cyano; formyl; trifluoromethyl; nitro; phenyl; straight-chain or branched $C_1$-$C_4$-alkoxy; straight-chain or branched $C_1$-$C_4$-alkoxycarbonyl; straight-chain or branched $C_1$-$C_4$-acyl; or optionally substituted straight-chain or branched $C_1$-$C_4$-alkyl wherein the substituents are hydroxyl, straight-chain or branched $C_1$-$C_4$-alkoxy, straight-chain or branched or a group of the formula —$NR^{18}R^{19}$, wherein $R^{18}$ and $R^{19}$ have the abovementioned meaning of $R^7$ and $R^8$ are identical to or different from these, or are substituted by a group of the formula —$CONR^9R^{10}$ or —$NR^{11}R^{12}$, wherein $R^9$ and $R^{10}$ are identical or different and denote hydrogen or methyl, $R^{11}$ and $R^{12}$ are identical or different and have the abovementioned meaning of $R^7$ and $R^8$ and are identical to or different from these, and/or the heterocyclic radicals are defined in A are substituted by a radical of the formula

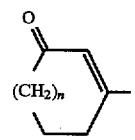

wherein n denotes the number 0, 1 or 2, or salt or S-oxide thereof.

4. The heteroaryl-oxazolidinone according to claim 1, which has the formula

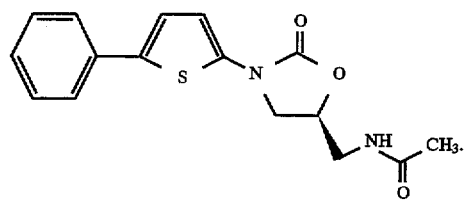

5. A pharamaceutical composition which comprises an effective amount of a compound according to claim 1 and an inert excipient.

6. A method of treating infections caused by bacteria or bacteria-like organisms in a host in need thereof, which comprises administering an effective amount of a compound according to claim 1 to said host.

* * * * *